(12) United States Patent
Kalmann et al.

(10) Patent No.: US 11,648,396 B2
(45) Date of Patent: *May 16, 2023

(54) EXTRACTOR FOR REMOVING A LEAD FROM A PATIENT

(71) Applicant: Talpanetics bv, Bunschoten-Spakenburg (NL)

(72) Inventors: Menno Kalmann, Elspeet (NL); Wieger Kaptein, Bunschoten-Spakenburg (NL); Amit Ben Dror, Zurit (IL)

(73) Assignee: TALPANETICS BV, Bunschoten-Spakenburg (NL)

( * ) Notice: Subject to any disclaimer, the term of this patent is extended or adjusted under 35 U.S.C. 154(b) by 624 days.

This patent is subject to a terminal disclaimer.

(21) Appl. No.: 16/724,312

(22) Filed: Dec. 22, 2019

(65) Prior Publication Data

US 2020/0121918 A1 Apr. 23, 2020

Related U.S. Application Data

(63) Continuation of application No. 15/655,773, filed on Jul. 20, 2017, now Pat. No. 10,532,207, which is a continuation of application No. 14/455,921, filed on Aug. 10, 2014, now Pat. No. 9,889,294.

(60) Provisional application No. 61/869,729, filed on Aug. 25, 2013.

(51) Int. Cl.
| | | |
|---|---|---|
| *A61N 1/36* | (2006.01) |
| *A61N 1/05* | (2006.01) |
| *A61B 17/3205* | (2006.01) |
| *A61B 17/34* | (2006.01) |
| *A61B 17/00* | (2006.01) |
| *A61N 1/372* | (2006.01) |

(52) U.S. Cl.
CPC ........ *A61N 1/056* (2013.01); *A61B 17/32053* (2013.01); *A61B 17/3468* (2013.01); *A61B 2017/00469* (2013.01); *A61N 1/372* (2013.01); *A61N 2001/0578* (2013.01)

(58) Field of Classification Search
CPC .......... A61B 17/32053; A61B 17/3468; A61N 1/372
See application file for complete search history.

(56) References Cited

U.S. PATENT DOCUMENTS

| | | | |
|---|---|---|---|
| 4,574,800 A | 3/1986 | Peers-Trevarton | |
| 4,576,162 A * | 3/1986 | McCorkle | A61N 1/057 606/174 |
| 4,582,056 A * | 4/1986 | McCorkle, Jr. | A61B 17/29 606/1 |
| 6,033,402 A | 3/2000 | Tu et al. | |
| 8,092,467 B1 | 1/2012 | Lindstrom | |
| (Continued) | | | |

FOREIGN PATENT DOCUMENTS

EP 1935348 6/2008

*Primary Examiner* — Eric D. Bertram
(74) *Attorney, Agent, or Firm* — Neil D. Gershon

(57) ABSTRACT

An extractor for removing an implanted lead from a patient, the extractor comprising a proximal portion, a distal portion, a lumen dimensioned to receive the lead therein, a cutter at the distal portion for cutting tissue adjacent the implanted lead, and a first clamping member movable between a clamping position to clamp the lead and an unclamping position to unclamp the lead. The extractor and lead are relatively movable to remove the lead.

20 Claims, 26 Drawing Sheets

(56) References Cited

U.S. PATENT DOCUMENTS

| | | | |
|---|---|---|---|
| 9,301,773 B2* | 4/2016 | Olomutzki | A61B 17/3205 |
| 9,889,294 B2* | 2/2018 | Kalmann | A61B 17/32053 |
| 10,207,105 B2* | 2/2019 | Kalmann | A61N 1/056 |
| 10,532,207 B2* | 1/2020 | Kalmann | A61N 1/056 |
| 2003/0092995 A1* | 5/2003 | Thompson | A61B 1/3137 |
| | | | 600/473 |
| 2004/0147996 A1 | 7/2004 | Miazga et al. | |
| 2008/0154293 A1 | 6/2008 | Taylor | |
| 2010/0198229 A1* | 8/2010 | Olomutzki | A61N 1/056 |
| | | | 606/129 |
| 2011/0106099 A1 | 5/2011 | Duffy et al. | |
| 2011/0178543 A1 | 7/2011 | Chin et al. | |
| 2013/0116704 A1* | 5/2013 | Geistert | A61B 17/0682 |
| | | | 606/129 |
| 2014/0288572 A1* | 9/2014 | Olomutzki | A61N 1/05 |
| | | | 606/129 |
| 2016/0374721 A1* | 12/2016 | Olomutzki | A61B 17/3205 |
| | | | 606/129 |
| 2017/0216574 A1* | 8/2017 | Booker | A61B 17/32053 |
| 2021/0186539 A1* | 6/2021 | Stein | A61B 17/3468 |

* cited by examiner

EXTRACTOR FOR REMOVING A LEAD FROM A PATIENT

This application is a continuation of application Ser. No. 15/655,773, filed on Jul. 20, 2017, now U.S. Pat. No. 10,532,207, which is a continuation of application Ser. No. 14/455,921, filed Aug. 10, 2014, now U.S. Pat. No. 9,889,294, which claims the benefit of U.S. Provisional Application No. 61/869,729 filed Aug. 25, 2013. The entire contents of each of these applications are incorporated herein by reference.

BACKGROUND

Technical Field

The invention relates to an extractor for removing an implanted lead from a patient, such as a cardiac pacing lead.

Background of Related Art

Recently, implantation of cardiac pacing devices has become a standard medical intervention for correcting cardiac rhythm thereby reducing patient's health complaints due to an abnormal cardiac condition.

The cardiac pacing device, such as a pacemaker, includes one or more electrical leads which supply a due electrical stimulus from the pacemaker or implantable cardioverter defibrillator to the heart muscle. These electrodes are implanted in the heart tissue, i.e., in a vein in the heart such as the superior vena cava or subclavia vena which may take place during open heart surgery. The distal portion of the electrical leads may include anchors for affixing the electrode lead inside the heart muscle. The electrode wire is covered with a suitable layer of insulator for electrical safety in operation. The leads can have an externally threaded tip to screw into the tissue.

During use, the electrical lead may be damaged or may need to be replaced due to maintenance considerations. This procedure is usually complicated by the fact that during the time the lead has dwelled inside the body, it has grown into a scar tissue as well as it may be covered by tissue as the result of tissue ingrowth. Tissue ingrowth can occur along various portions of the lead. It is appreciated that both phenomena make it difficult to remove the electrode lead from the heart tissue. This is especially the case since the vein makes a curve from the pacemaker to the heart and the lead is often attached to the vein at this curve, thereby making release difficult.

Through the years different attempts have been made to provide a suitable lead extractor device which is capable of removing an implanted electrical lead without causing damage to the patient.

Originally, lead extractors were mechanical devices operable by a cardiac surgeon to free the leads from the surrounding tissue for removing them from the heart. The disadvantage of such devices is that a mechanical force is initially applied in the region of a manifold of the lead extractor and has to be suitably transferred to a distant location along the lead for freeing it from the tissue. Usually the lead extraction is carried out using a subclavian approach or femoral approach. In both approaches a sheath is placed over the lead and is threaded over the lead to reach the distal portion, i.e., the tip, of the lead. However, it has been clinically found that such mechanical approach has a high risk of undesirable disruption of the tissue of the patient when attempting to free the implanted electrode lead from the heart muscle. Also, the hardened tissue around the lead can in some instances make placement of the sheath difficult.

A particular version of a lead extractor is disclosed in U.S. Pat. No. 4,574,800, which is arranged to remove implanted leads from a patient by grasping the lead substantially close to its implantation position. Accordingly, this extractor device includes an elongate tubular member arranged to slide into and through a longitudinal lumen of the cardiac pacing lead. The distal portion of the elongate tubular member comprises a protrusion member adapted to provide a wedging surface. The wedging surface is effected by a tapering proximal surface of the protrusion member. The proximal tapering surface may take the form of a spherical or a conical section. The elongate tubular member further includes a spherical gripping member arranged to engage with the lead. When the proximal end portion of the elongate member is pulled with a substantial force, for example, by suitable actuation of the handle, the protrusion member forms a flared distal end section of the elongate tubular member. The elongate tubular member has a length such that it projects beyond the proximal end of the cardiac lead when the known extractor is fully inserted into the lead. In use, the extractor assembly is inserted into and through the cardiac pacing lead until the protrusion member abuts the proximal end of the implanted electrode. Afterwards, the protrusion member is activated to cause the distal portion of the tubular member to wedge. The wedged portion comes into frictional engagement with the inside surface of the distal portion of the cardiac pacing lead. Finally, a pulling force is applied to the proximal portion of the elongate tubular member, which is transmitted to the distal portion of the elongate tubular member towards the flared portion. This pulls the cardiac pacing lead from its dwelling.

Although in the foregoing system's excessive force to the electrode wire and its insulator sheath may be avoided, the pulling forces, which are transferred from the proximal end of the lead extractor, may cause undesirable local damage to the tissue. Additionally, since the lead extractor is provided inside the lumen of the lead, it has to meet stringent constraints regarding its permissible dimensions. This limits the possibilities of optimization of the lead extractor in terms of mechanics.

Other prior art attempts to extract leads involve inserting a tube over the lead and drilling down with the tube to separate surrounding tissue from the external surface of the lead to free the lead. Still other prior art methods include utilizing lasers or electrosurgical energy, such as radiofrequency energy at the end of a catheter to sever the tissue.

The need exists for a simplified and less traumatic approach to removing leads, such as cardiac leads, from a patient.

SUMMARY

The present device provides an improved lead extractor which is capable of secure removal of the implanted leads, such as cardiac leads, causing minimum damage to the patient's tissue. The lead is clamped by the extractor and incremental relative movement of the lead and retractor moves the lead within the extractor lumen as tissue surrounding the lead is cut (dissected) by the extractor.

In one aspect, the present invention provides an extractor for removing an implanted lead from a patient, the extractor comprising a proximal portion, a distal portion, a lumen dimensioned to receive the lead therein, and a cutter at the distal portion of the extractor for cutting tissue adjacent the implanted lead. A first clamping member is spaced proximally of the cutter, the first clamping member movable between a clamping position to clamp the lead and an unclamping position to unclamp the lead, and the extractor and lead are relatively movable to remove the lead.

In some embodiments the extractor further includes a movement mechanism operatively associated with the first clamping member, the movement mechanism movable between proximal and distal positions to alter an orientation of the first clamping member to move it between the clamping and unclamping positions.

In some embodiments, the first clamping member includes a first pivotable ring member having an opening therethrough to receive the lead therethrough, wherein the first pivotable ring member is tiltable relative to a longitudinal axis of the lead to apply a clamping force on the lead to clamp the lead when in a more tilted position. The extractor can further include a second pivotable clamping member, and the second clamping member can comprise a second ring member axially spaced from the first ring member and having an opening therethrough to receive the lead therethrough and tiltable relative to the longitudinal axis of the lead to apply a clamping force on the lead to clamp the lead when in a more tilted position. In some embodiments, the first and second pivotable ring members are alternatively movable between the clamped and unclamped positions so that the first pivotable ring member clamps the lead while the second pivotable ring member is in an unclamped position to allow relative movement of the lead therethrough and the second pivotable ring member clamps the lead while the first pivotable ring member is in an unclamped position to allow relative movement of the lead therethrough.

In some embodiments, the extractor further includes a housing and a carrier slidably mounted within the housing, the first clamping member positioned within the carrier, and axial movement of the carrier moves the first clamping member axially. In some embodiments, movement of the carrier in a proximal direction moves the lead further in the lumen of the extractor. In some embodiments, the extractor further includes a second clamping member positioned distal of the carrier.

In some embodiments, the extractor includes a second clamping member, wherein the first clamping member has a first hinge and the second clamping member has a second hinge, the first and second hinges radially spaced from a longitudinal axis of the extractor and lying on opposing sides of the longitudinal axis of the extractor.

The extractor can further include a cable operatively associated with the first clamping member, wherein distal movement of the cable advances the first clamping member distally and proximal movement of the cable retracts the first clamping member proximally.

The extractor can include a second clamping member and a stop to limit distal travel of the second clamping member, wherein the stop can be overridden to release the first and second clamping members.

In some embodiments, the cutter is both axially movable and rotatable concurrently with axial movement of the first clamping member. In some embodiments, the extractor further comprises an outer tube or housing, the cutter positioned at a distal portion of the outer tube and the outer tube having a helical slot for rotational movement of the outer tube.

In some embodiments, the extractor includes a second clamping member, wherein movement of the extractor is effected by alternate movement of the first and second clamping members to incrementally move the lead and extractor relative to one another as the tissue is cut, e.g., severed and/or dissected, by the cutter.

In some embodiments, the movement mechanism is controlled by an external power source connected to the movement mechanism.

In some embodiments, a flexible sheath is provided which is rotatable with respect to the extractor to unscrew a distal tip of the lead from tissue.

In another aspect, the present invention provides an extractor for removing an implanted lead from a patient, the extractor having a proximal portion, a distal portion, a lumen to receive the lead therein, and a cutter at the distal portion for cutting tissue adjacent the implanted lead. The extractor and lead are incrementally relatively movable to swallow the lead as tissue is cut by the cutter adjacent the lead.

In some embodiments, the extractor includes a first clamping member, and the cutter rotates to cut tissue as the position of the first clamping member changes. In some embodiments, the first clamping member is movable between unclamped position and clamped positions, and in the clamped position retraction of the first clamping member causes swallowing of the lead by the extractor. In some embodiments, the first clamping member is tiltable relative to a longitudinal axis of the extractor to move between the clamped and unclamped positions.

The extractor can include in some embodiments a second clamping member movable between unclamped position and clamped positions, and in the clamped position retraction of the second clamping member causes swallowing of the lead by the extractor, the first and second clamping members alternately moved between clamped and unclamped positions. The extractor can further include a second clamping member movable between unclamped and clamped positions, wherein the first clamping member has a first hinge and the second clamping member has a second hinge, the first and second hinges radially spaced from a longitudinal axis of the extractor and lying on opposing sides of the longitudinal axis of the extractor, wherein relative movement of the lead and extractor causes pivoting of the first and second clamping members.

The extractor can include a carrier for moving the first clamping member, the carrier including an engagement tab to engage a slot in a housing containing the cutter, wherein movement of the carrier concurrently causes pivoting of the first clamping and rotation of the housing to rotate the cutter.

In accordance with another aspect, the present invention provides an extractor for removing an implanted lead from a patient, the extractor having a lumen to receive the lead and first and second clamping members, the clamping members movable between unclamped positions where the lead can freely move within the lumen and clamped positions to frictionally engage the lead, wherein relative movement of the extractor and lead effects pivotable movement of the clamping members.

In some embodiments, further relative movement of the extractor and lead causes further frictional force by the first clamping member on the lead. In some embodiments, the first clamping member has a first hinge and the second clamping has a second hinge, the first and second hinges radially spaced from a longitudinal axis of the extractor and lying on opposing sides of the longitudinal axis of the extractor.

The extractor can include a movement mechanism for axially moving the first clamping member, wherein such axial movement rotates a cutter of the extractor.

The first and second clamping members can in some embodiments be spring biased to the clamped positions.

In some embodiments, relative movement of the extractor and lead occurs in discrete increments which progressively swallow the lead within the lumen of the extractor.

In accordance with another aspect of the present invention, a method of removing an implanted lead from a patient is provided comprising:
   a) providing an extractor having a lumen to receive the lead and a cutter at a distal portion;
   b) positioning the extractor so the lead extends through the lumen of the extractor and the cutter is adjacent or in contact with the tissue adjacent the lead;
   c) moving a first clamping member of the extractor in a first direction to relatively move the extractor and lead to swallow the lead; and
   d) cutting tissue adjacent the lead by the cutter.

In some embodiments, the step of cutting tissue includes rotating the cutter. In some embodiments, rotation of the cutter occurs concurrently with movement of the first clamping member.

The method can further include the steps of moving a second clamping member to clamp the lead, and the unclamping the first clamping member before the step of moving the second clamp member proximally and unclamping the second clamping member before the step of moving the first clamping member to thereby provide incremental relative movement of the lead and extractor. The method can further comprise the step of moving a second clamping member proximally to swallow the lead.

In some embodiments, the first clamping member is released after the second clamping member is moved to clamp the lead, and the second clamping member is released after the first clamping member is moved to clamp the lead.

In some embodiments, the step of moving the first clamping member includes the step of tilting the first clamping member with respect to a longitudinal axis of the extractor so it moves from a first angle to a second different angle.

In some embodiments, the extractor has a second clamping member, and the first and second clamping members each have an opening to receive the lead therethrough and changing angles of the first and second clamping members with respect to a longitudinal axis of the extractor changes the angle of the first and second openings to clamp the lead.

The method may further include the step of rotating a flexible sheath to rotate the lead to unscrew a distal end of the lead from tissue.

BRIEF DESCRIPTION OF THE DRAWINGS

Preferred embodiment(s) of the present disclosure are described herein with reference to the drawings wherein:

FIGS. 12A-12F illustrate side views (with the housing shown in phantom) to show the method of use of the lead extractor of FIG. 2 wherein:

FIG. 12A illustrates the lead extractor in the neutral position with the proximal and distal clamp rings in the substantially perpendicular position;

FIG. 12B illustrates a first cable pulled proximally to move the distal clamp ring to the angled position;

FIG. 12C illustrates the first cable pulled further proximally to move the lead proximally;

FIG. 12D illustrates a second cable pulled proximally to move the proximal clamp ring to the angled position;

FIG. 12E illustrates the first cable released to return the distal clamp ring to its substantially perpendicular and distal position;

FIG. 12F illustrates the second cable pulled further proximally to move the lead further proximally;

FIGS. 13A-13D are side views of the lead extractor of FIG. 2, with the internal rings and spring shown in phantom, illustrating how the lead and extractor are relatively moved to cut tissue about the lead wherein:

FIG. 13A illustrates the lead extractor being inserted over an implanted lead to approach the tissue surrounding the lead, the lead extractor shown in the neutral position with the proximal and distal clamp rings in the substantially perpendicular position;

FIG. 13B illustrates the first cable pulled proximally to move the lead proximally and sever the surrounding tissue;

FIG. 13C illustrates a second cable pulled proximally to move the proximal clamp ring to the angled position;

FIG. 13D illustrates the first cable released to return the distal clamp ring to its substantially perpendicular position and the second cable pulled further proximally to move the lead further proximally with the surrounding tissue being severed;

FIGS. 18A-18D are side views of the lead extractor of FIG. 17, with the sheath shown in cross-section, illustrating how the lead and extractor are relatively moved to cut tissue about the lead wherein:

FIG. 18A illustrates the lead extractor being inserted over an implanted lead to approach the tissue surrounding the lead, the lead extractor shown in the neutral position with the proximal and distal clamp rings in the substantially perpendicular position;

FIG. 18B illustrates the first cable pulled proximally to move the lead proximally and sever the surrounding tissue;

FIG. 18C illustrates a second cable pulled proximally to move the proximal clamp ring to the angled position; and FIG. 18D illustrates the first cable released to return the distal clamp ring to its substantially perpendicular position and the second cable pulled further proximally to move the lead further proximally with the surrounding tissue being severed.

DETAILED DESCRIPTION OF EMBODIMENTS

The lead extractor disclosed herein advantageously holds the lead adjacent the area where the tissue cutting (severing and/or dissecting) occurs, thereby transferring the power of the work required to the location where it is needed. This provides an advantage over prior lead extractors where the extractor is held and maneuvered from a proximal end to apply a cutting or dissecting force to the tissue at the remote distal end. Thus, the lead extractor of the present invention provides for lead removal with minimal damage to the patient's tissue.

To this end, the present disclosure provides a lead extracting device which grips and frictionally retains the lead, and then incrementally moves relative to the lead, cutting the surrounding tissue as it is moved proximally within the device. Note the lead and extractor move relative to each other. That is, if the distal end of the lead is fixed, the relative movement will occur by the extractor being advanced along the lead. If the distal end of the lead is not fixed, relative movement will occur by the lead moving proximally within the extractor. Also, relative movement can include proximal movement of the lead simultaneous with distal movement of the extractor. In any case, as a result of this relative movement, the extractor "swallows" the lead within its lumen as it incrementally and progressively cuts through tissue around the lead to free the lead from the tissue. Cutting of tissue can occur by severing and/or dissecting tissue. The cutter is shown as part of the housing in the embodiments herein, however, alternatively the cutter can be a separate component attached to the housing.

Figure 1:
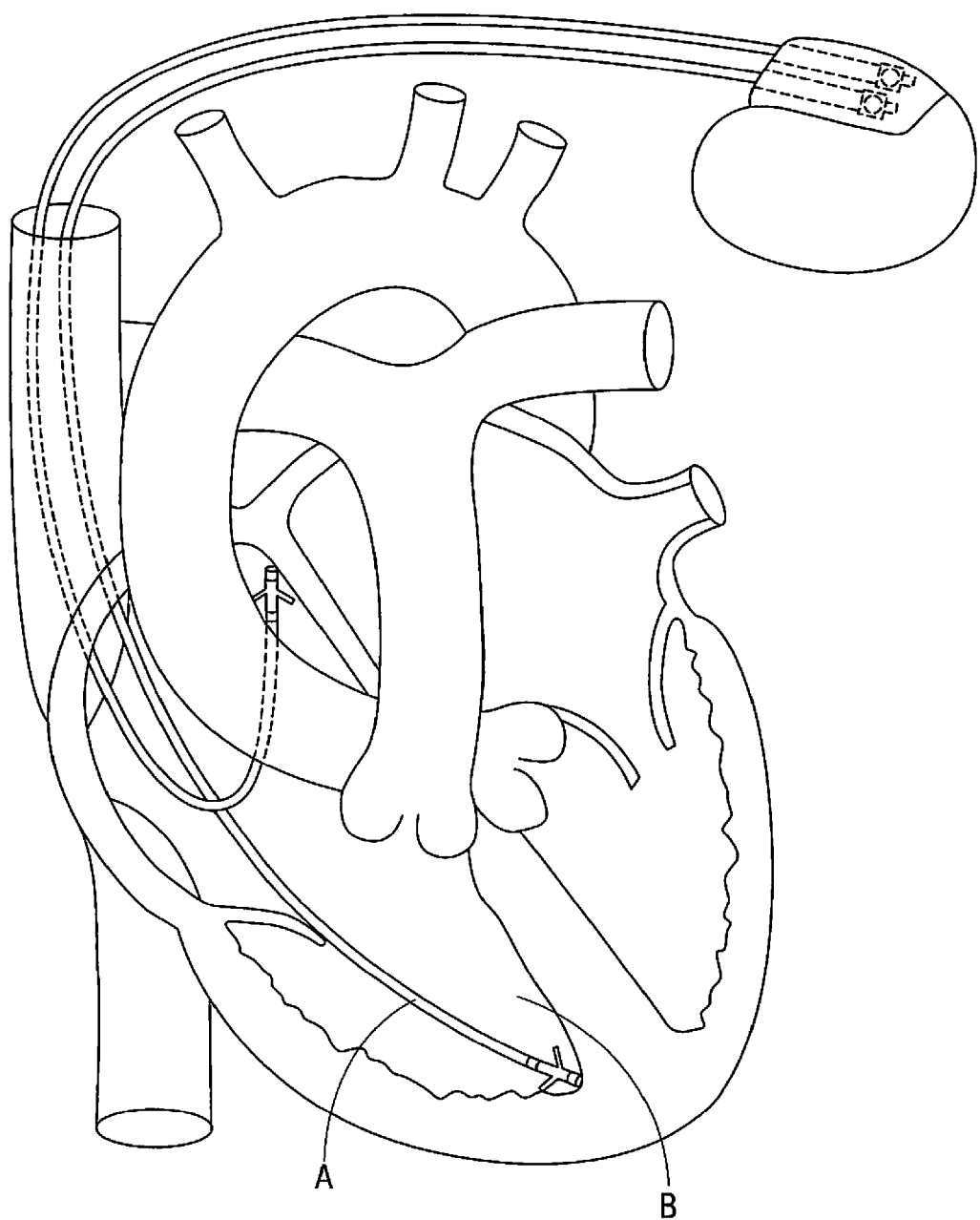
FIG. 1 illustrates a patient's anatomy showing an implanted cardiac lead to be removed.
Figure 2:
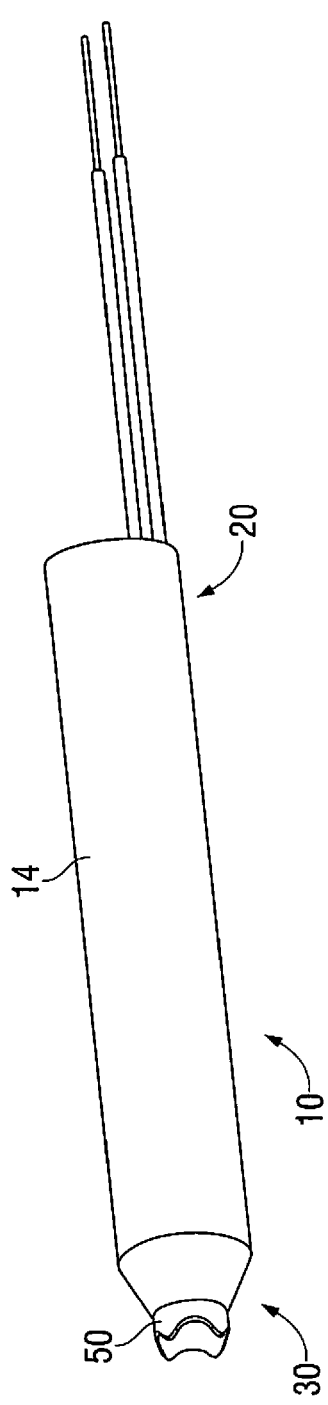
FIG. 2 is a perspective view of one embodiment of the lead extractor of the present disclosure.
Figure 3:
FIG. 3 is a perspective view of the lead extractor of FIG. 2 positioned over the cardiac lead.
Figure 4:
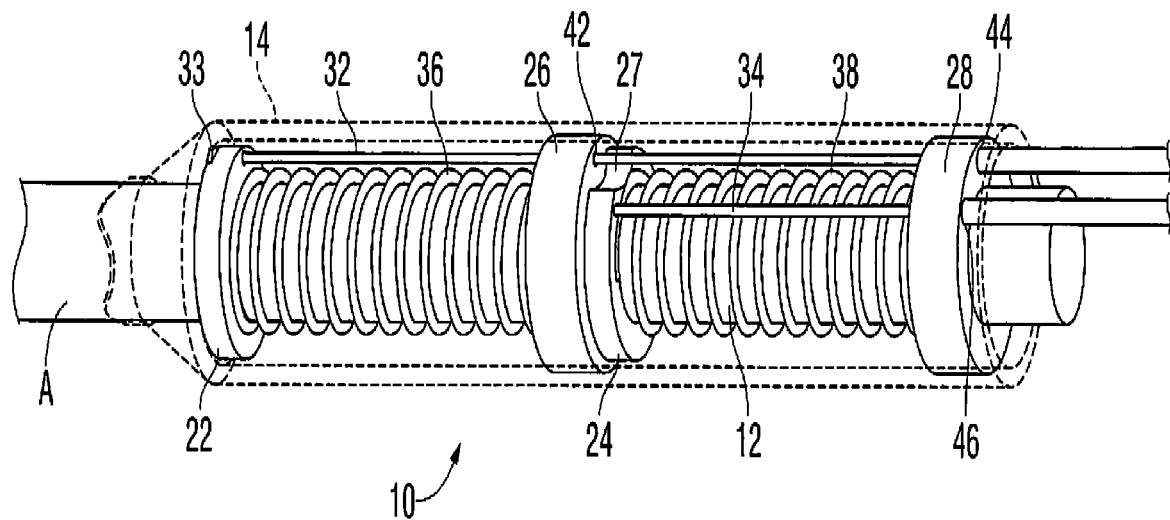
FIG. 4 is a side view of the lead extractor of FIG. 2 with the outer housing shown in phantom to illustrate the internal rings and springs, the extractor shown in the neutral position.
Figure 5:
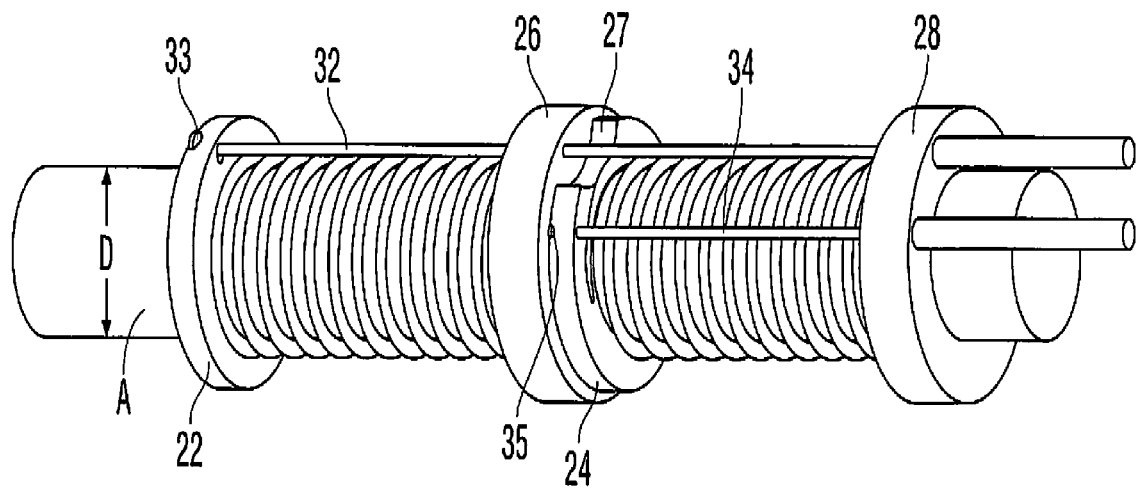
FIG. 5 is a side perspective view similar to FIG. 4 with the housing removed for clarity.

With reference to FIGS. 2, 4 and 5, the lead extracting device is designated generally by reference numeral 10 and includes an outer housing or body 14 and an internal tubular member or inner body 12 having a lumen dimensioned to receive a lead therein. The outer housing (outer tube) 14 has a proximal end 20 and a distal end 30. As used herein the term "proximal" refers to the portion that is closer to the user and the term "distal" refers to the portion that is further from the user. A cutting knife (cutter) or cutting portion 50 is positioned at the distal end 30 of outer housing 14 configured to cut tissue surrounding the lead, designated by reference letter "A". FIG. 1 illustrates an anatomical view of the heart, illustrating the location of the cardiac lead A which is desired to be removed from the right ventricle B. It should be appreciated that the devices disclosed herein are described for removing a cardiac lead, however, it should be understood that the device also has other surgical applications. Note tissue ingrowth around the lead also occurs at regions along the length of the lead proximal of the distal tip of the lead.

The lead extractor includes a distal clamping ring 22, a proximal clamping ring 24, a distal fixed ring 26 and a proximal fixed ring 28. A first actuator or actuating (movement) mechanism in the form of a first wire or cable 32 is operably connected to the distal clamping ring 22 and a second actuator or actuating mechanism in the form of a second wire or cable 34 is operably connected to the proximal clamp ring 24. The cable 32 is operable to pivot distal clamping ring 22 from a substantially perpendicular position to an angled position with respect to the longitudinal axis of the extractor 10. In the substantially perpendicular position, the extracting device 10 is freely movable over the lead A. In the angled (tilted) or oblique position, due to the dimension of the opening in the distal clamping ring 22, the distal clamping ring 22 frictionally engages, i.e., clamps, the external surface of the lead A as the surface around the opening in the clamping ring 22 frictionally engages the outer surface of the lead. Such clamping allows relative movement of the lead, i.e., "swallowing" of the lead described in detail below. Similarly, the cable 34 is operable to pivot proximal clamp ring 24 from a substantially perpendicular position to an angled position with respect to the extractor 10. In the substantially perpendicular position, the extracting device 10 is freely movable over the lead A. In the angled (tilted) or oblique position, due to the dimension of the opening in the proximal clamping ring 24, the proximal clamping ring 24 frictionally engages, i.e., clamps, the external surface of the lead A as the surface around the opening in the clamping ring 24 frictionally engages the outer surface of the lead. Such clamping allows relative movement of the lead, i.e., "swallowing" of the lead as described in detail below. A distal spring 36 is positioned around tubular member 12 to bias the distal clamp ring 22 in a distal direction and a proximal spring 38 is positioned around tubular member 12 to bias the proximal clamp ring 24 in the distal direction.

Figure 10:
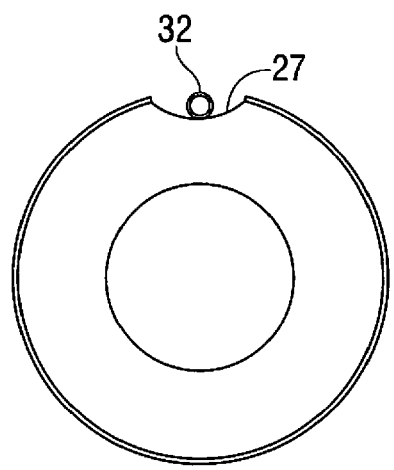
FIG. 10 is a front view illustrating the cable extending through the notch in the proximal clamp ring.

First cable 32, also referred to herein as the distal ring cable, is fixedly attached to distal ring 22 (at connection 33), extends through an aperture 42 in the distal fixed ring 26 and an aperture 44 in proximal fixed ring 28. Proximal clamp ring 24 has a cutout or notch 27 to accommodate the first cable 32 (see also FIG. 10). The cable 32 extends proximally to a position outside the patient for manipulation manually by a user or alternatively for connection to a motor as described below.

Cable 34, also referred to herein as the proximal ring cable, is fixedly attached to proximal ring 24 (at connection 35) and extends through an aperture 46 in the proximal fixed ring 26. The cable 34 extends proximally to a position outside the patient for manipulation manually by a user or alternatively for connection to a motor. The cables 32 and 34 thereby provide a movement mechanism for the clamping members.

Figure 6:
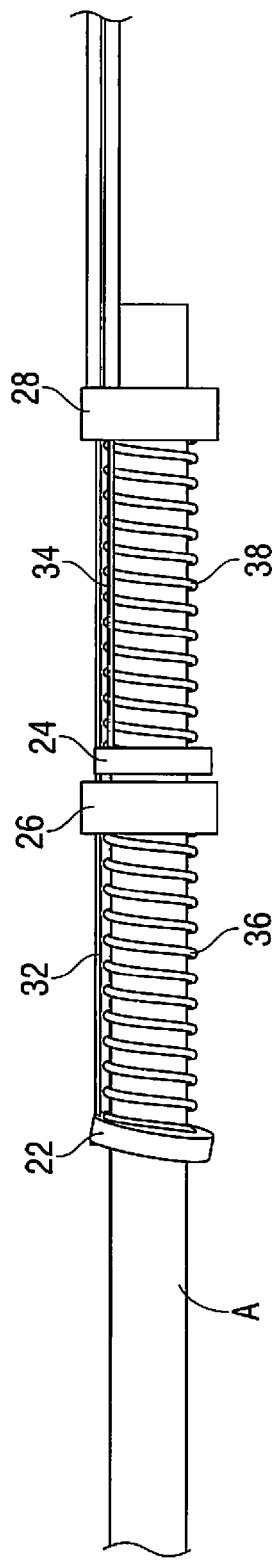
FIG. 6 is a side view of the lead extractor of FIG. 2 showing the distal clamp ring moved to the angled position.
Figure 7:
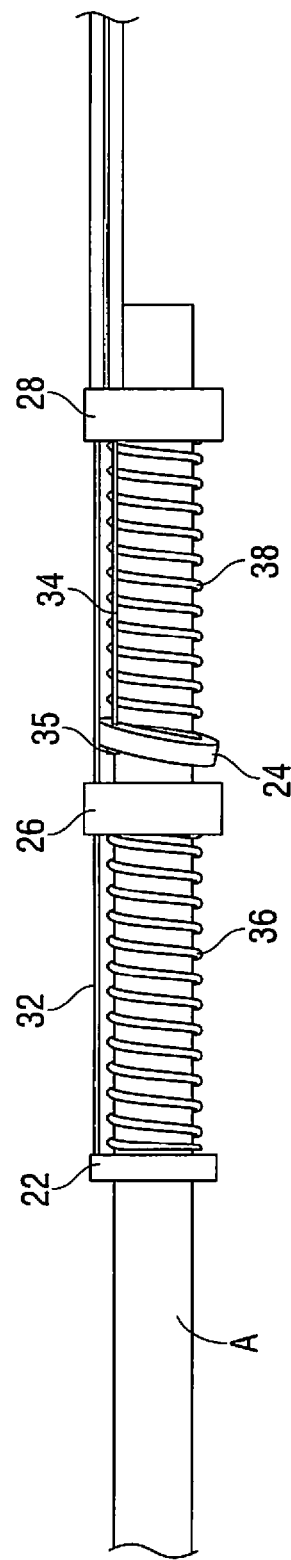
FIG. 7 is a side view similar to FIG. 6 showing the proximal clamp ring moved to the angled position.

The extractor 10 preferably has three operable positions. In a first or initial position, referred to as the neutral or zero position, both the distal and proximal clamping rings 22, 24 are in the substantially perpendicular position in which they do not frictionally retain the cardiac lead and therefore the device 10 can be slidably moved over the lead A, as the lead A extends through the lumen of the tubular member 12. In this neutral position, this sliding movement is obtained since the inside diameter of the opening in the distal ring and the inside diameter of the opening in the proximal ring 22 is greater, e.g., slightly greater, than the outside diameter D of the lead A. Note this neutral position also enables the device 10 at any time during the procedure to release the lead and be adjusted or removed from the lead and patient. In the second position, the distal ring 22 is moved to the angled position to engage (clamp) the lead A while the proximal ring 24 remains in the substantially perpendicular position, as shown in FIG. 6. In the third position, the proximal ring 24 is moved to the angled position to engage (clamp) the lead A while the distal ring 22 remains in the substantially perpendicular position, as shown in FIG. 7. It should be appreciated that alternatively, the second position can denote when the proximal ring 22 is moved to the angled position to engage the lead A and the distal ring 24 remains in the substantially perpendicular position, in which case the third position would denote the position wherein the distal ring 22 is moved to the angled position to engage the lead A while the proximal ring 24 remains in the substantially perpendicular position.

Figure 8:
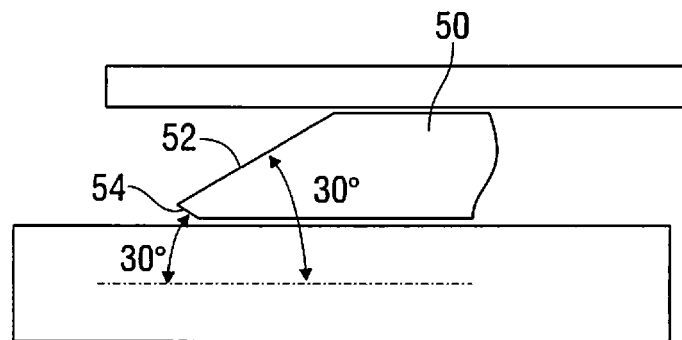
FIG. 8 is a close up view a portion of the cutter (knife) of the housing for cutting tissue.
Figure 9:
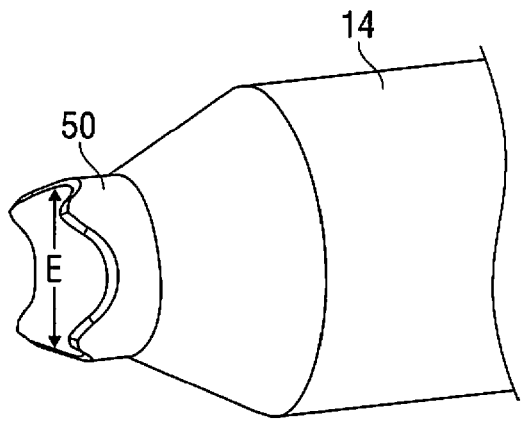
FIG. 9 is a close up view of the distal end of the housing of FIG. 2.

The knife (cutter) 50 preferably has an angled cutting edge that avoids the knife cutting into the vessel wall. The cutting edge is beveled at end 52, and has a small cutting edge 54 (FIG. 8), extending at an opposite angle to the bevel, thereby preventing the knife 50 from going into the lead. The knife 50 has a circular design with a sinuous shape, thereby providing a curved knife to perform a relative movement from the cutting edge to the tissue as in a guillotine-like action. The angles shown in FIG. 8 are by way of example as other angles are also contemplated. The inner diameter E of the knife 50 (FIG. 9) preferably is slightly greater than the outer diameter of the lead A to be received in the lumen of device 10.

Turning now to the method of use, and with reference to FIGS. 12A-12F, the device 10 is inserted over the lead A and advanced over the lead A until the knife 50 at the distal end 30 of the tubular member 12 is at the desired site, namely the site where the lead A is embedded or surrounded by tissue so it cannot be removed. This is typically proximal of the distal tip of the lead. In this position, the device 10 is ready for lead extraction.

Figure 12A:
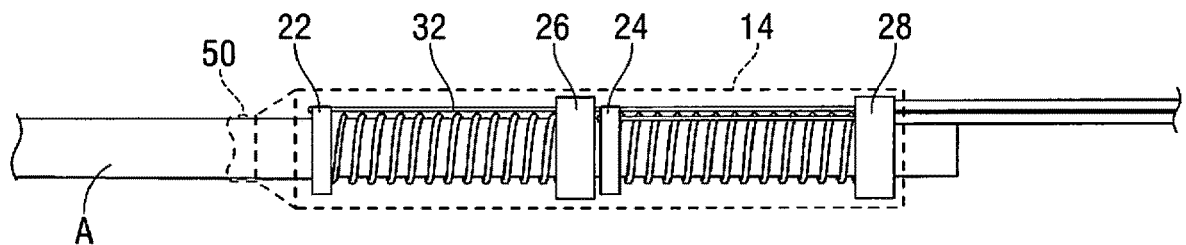
Figure 12B:
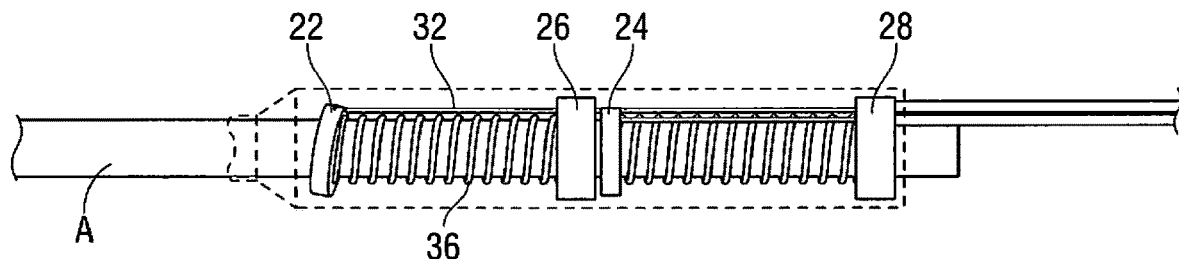
Figure 12C:
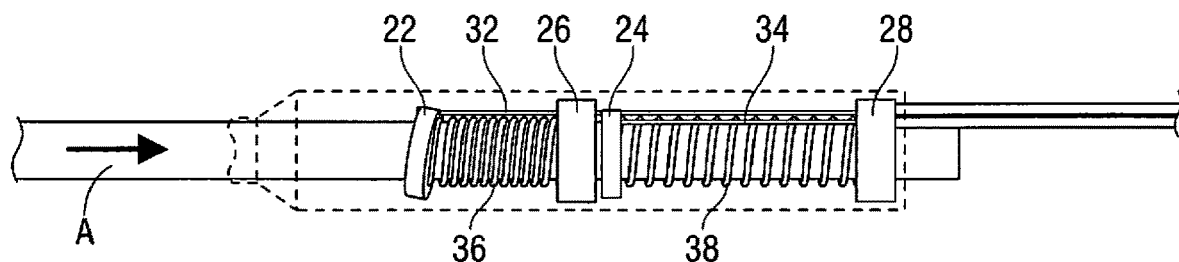
Figure 12D:
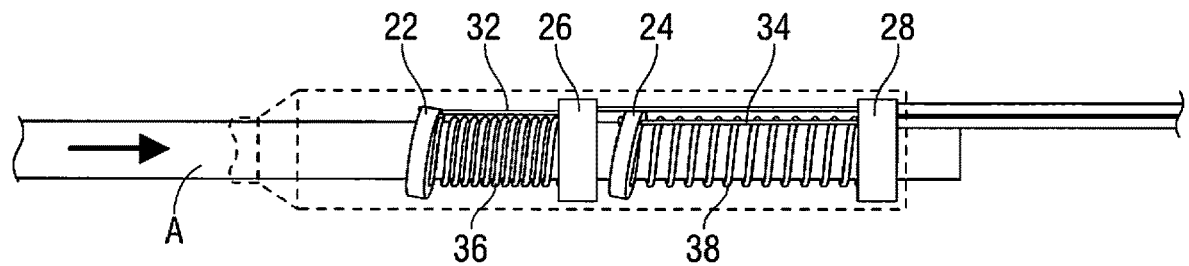

The user than pulls cable 32 proximally, or if motor operated, turns on the motor which automatically pulls the cable 32 proximally. In the first proximal movement of the cable 32, the distal clamping ring 22 is pivoted to its angled position of FIG. 12B to frictionally clamp or grasp the lead A. Upon further movement of the cable 32, the lead A is pulled back due to its frictional engagement with the device 10 via distal clamp ring 22 as shown in FIG. 12C and/or the device 10 is moved over the lead in this relative movement to "swallow" the lead A. (Since the proximal ring 24 is in its substantially perpendicular or non-engaging position, the lead can move through the opening in the ring 24). As the lead A is moved back proximally in the direction of the arrow of FIG. 12C it begins to be freed from tissue as the surrounding tissue is engaged and cut (severed and/or dissected) by knife 50. As can be appreciated, the cutting of tissue occurs adjacent the end of the device where the lead is engaged, thus providing more leverage and easier severing of the tissue. As the distal ring 22 is pulled proximally (rearwardly), it compresses distal spring 36. In an exemplary embodiment, distal clamping ring 22 is pulled back a maximum of approximately halfway to the distal fixed ring 26. In an exemplary embodiment, the distance between distal clamping ring 22 and distal fixed ring 26 is about 20 mm and the distal clamping ring 22 is pulled proximally about 10 mm thereby moving the lead A proximally about 10 mm in the direction of the arrow of FIG. 12C. Other distances are also contemplated.

Figure 12E:
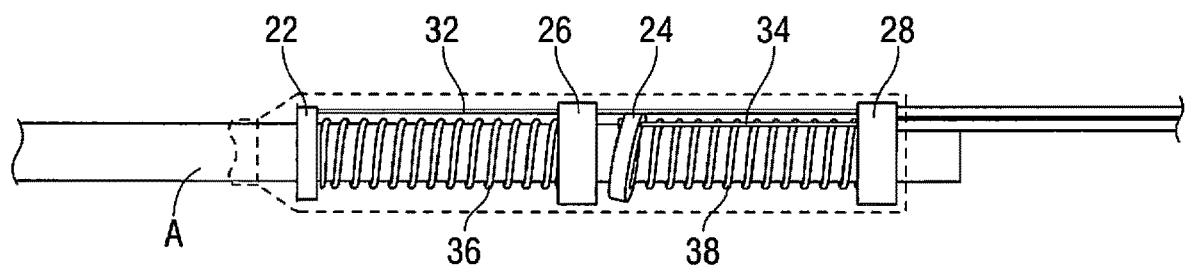

Once the distal clamping ring 22 has been pulled back to relatively move the lead A proximally or "swallow" the lead a predetermined amount, the second cable 34 can now be actuated. The user pulls cable 34 proximally, or if motor operated, the motor automatically pulls the cable 34 proximally after the first cable 32 has been pulled. In the first proximal movement of the cable 34, the proximal clamping ring 24 is pivoted to its angled position of FIG. 12D to frictionally clamp or grasp the lead A. Once the cable 34 has moved the proximal ring 32 to its angled position, the tension on the first cable 34 is released so the distal ring 22 can return to its substantially perpendicular or non-engaged position, aided by the force of distal spring 36 (FIG. 12E). In a preferred embodiment, the first cable 32 (and thus the distal clamp ring 22) is not released until the second cable 34 has been tensioned to move the proximal ring 24 to engage the lead A. This helps prevent slippage, e.g., distal movement of the lead A, since the lead A is continuously being grasped, albeit by alternating the grasping function between the proximal and distal clamping rings 22, 24.

Figure 12F:
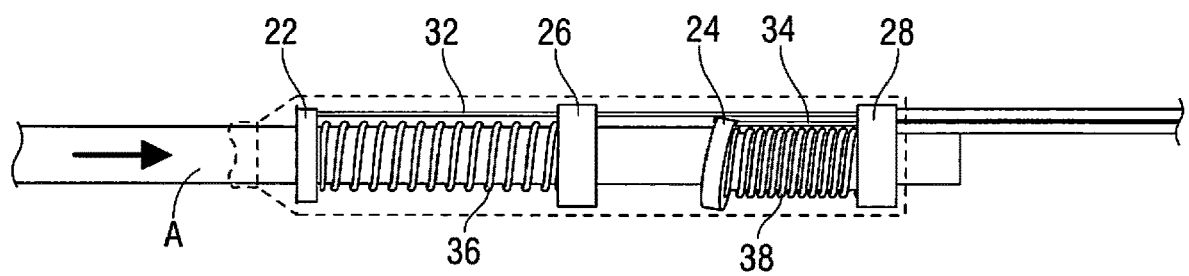

After the cable 34 has been pulled to pivot the proximal clamping ring 24 to its angled position, further retraction of the cable 34 pulls the lead A back (proximally) or moves the device 10 distally due to its frictional engagement with the device 10 via distal clamp ring 24. Thus, the lead A is relatively moved further back proximally in the direction of the arrow to further free it from surrounding tissue as the tissue is cut by knife 50 as shown in FIG. 12F. As the proximal ring 22 is pulled proximally (rearwardly), it compresses proximal spring 38. In an exemplary embodiment, proximal ring 22 is pulled back a maximum of approximately halfway to the proximal fixed ring 28. In an exemplary embodiment, the distance between proximal clamp ring 24 and proximal fixed ring 28 is about 20 mm and the proximal clamp ring 24 is pulled proximally about 10 mm, thereby relatively moving the lead A about 10 mm. Other distances are also contemplated.

Next, the first cable 32 is pulled to once again pivot the distal ring 22 to the angled engaging position. Once pulled, the second cable 34 can now be released, followed by further retraction of the first cable 32, to move the lead proximally due to its frictional engagement. After such movement, the second cable 34 is pulled proximally, followed by release of the first cable 34, and then further pulling of the cable 34 to move the lead A still further proximally and to continuously sever the surrounding tissue by knife 50. This step of alternatively pulling of the cables 32, 34 is repeated until the lead A is freed from the tissue and can be removed (with or separately from the device 10) from the tissue. This alternating cable motion can also be referred to as an oscillating movement in that the pulling of the cable alternates between the first and second cables, to incrementally pull the lead proximally or advance the extractor distally. This alternating action can also be considered as a step by step progressive "swallowing" of the lead. It can also be considered a tunneling action as it tunnels through tissue to separate tissue from the lead.

Figure 13A:
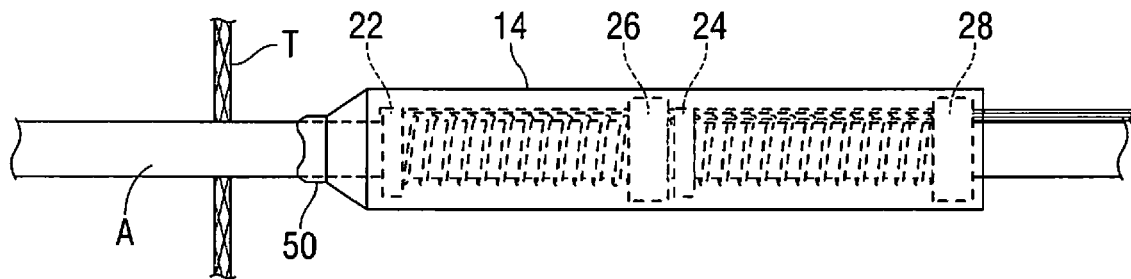
Figure 13B:
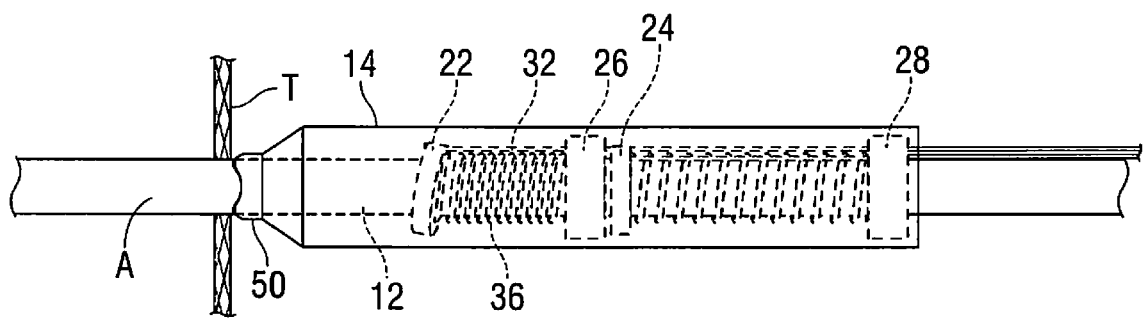
Figure 13C:
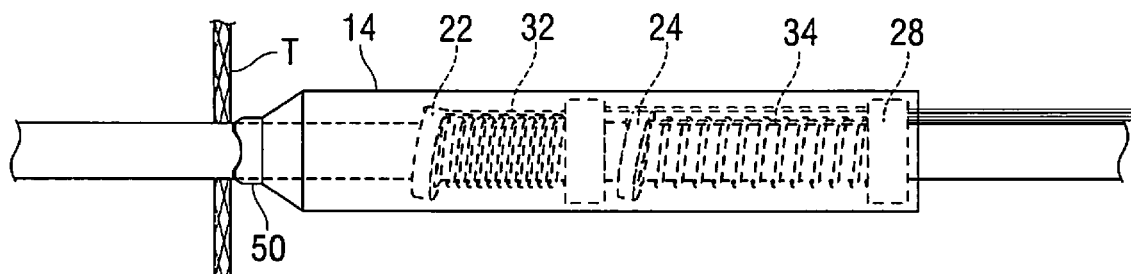
Figure 13D:
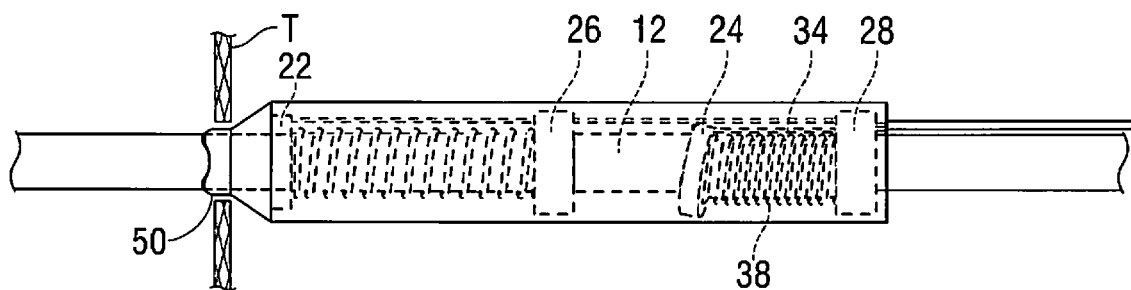

FIGS. 13A-13D illustrate how the lead is pulled back relative to tissue T. FIG. 13A shows the lead extractor being inserted over lead A to the position where the lead is captured by tissue T. After positioning of the extractor 10 in the desired position, the first cable 32 is pulled rearwardly and the lead A is retracted or the device 10 advanced as described above, with the tissue T engaging the cutting edge of knife 50 to cut the tissue surrounding the lead A to thereby free the lead (see FIG. 13B). In FIG. 13C, the proximal clamp ring 24 is angled by the pulling of the second cable 34. The first cable 32 is then released, and the proximal cable 34 is pulled back further to further move the lead proximally or advance the device 10, thereby causing the tissue to again be into contact with the knife 50 to cut the tissue. As explained herein, this keeps being repeated so that the knife 50 can continue to cut the tissue as the lead A is incrementally and progressively pulled rearwardly or swallowed within the lumen of tube 12 of the lead extractor 10.

Figure 14:
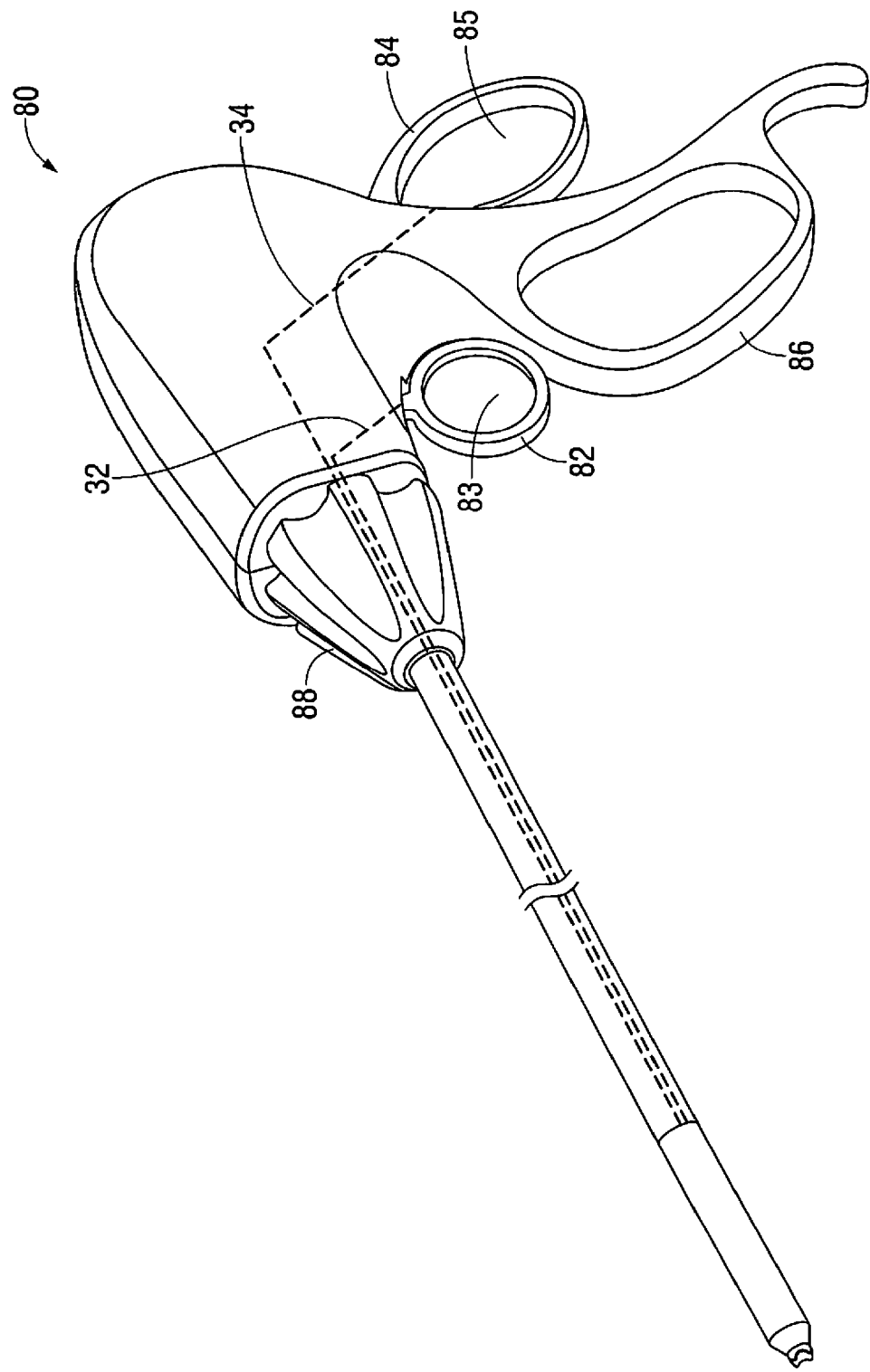
FIG. 14 is a perspective view of an alternative embodiment utilizing a manual control to actuate the cables of the extractor of FIG. 2.
Figure 15:
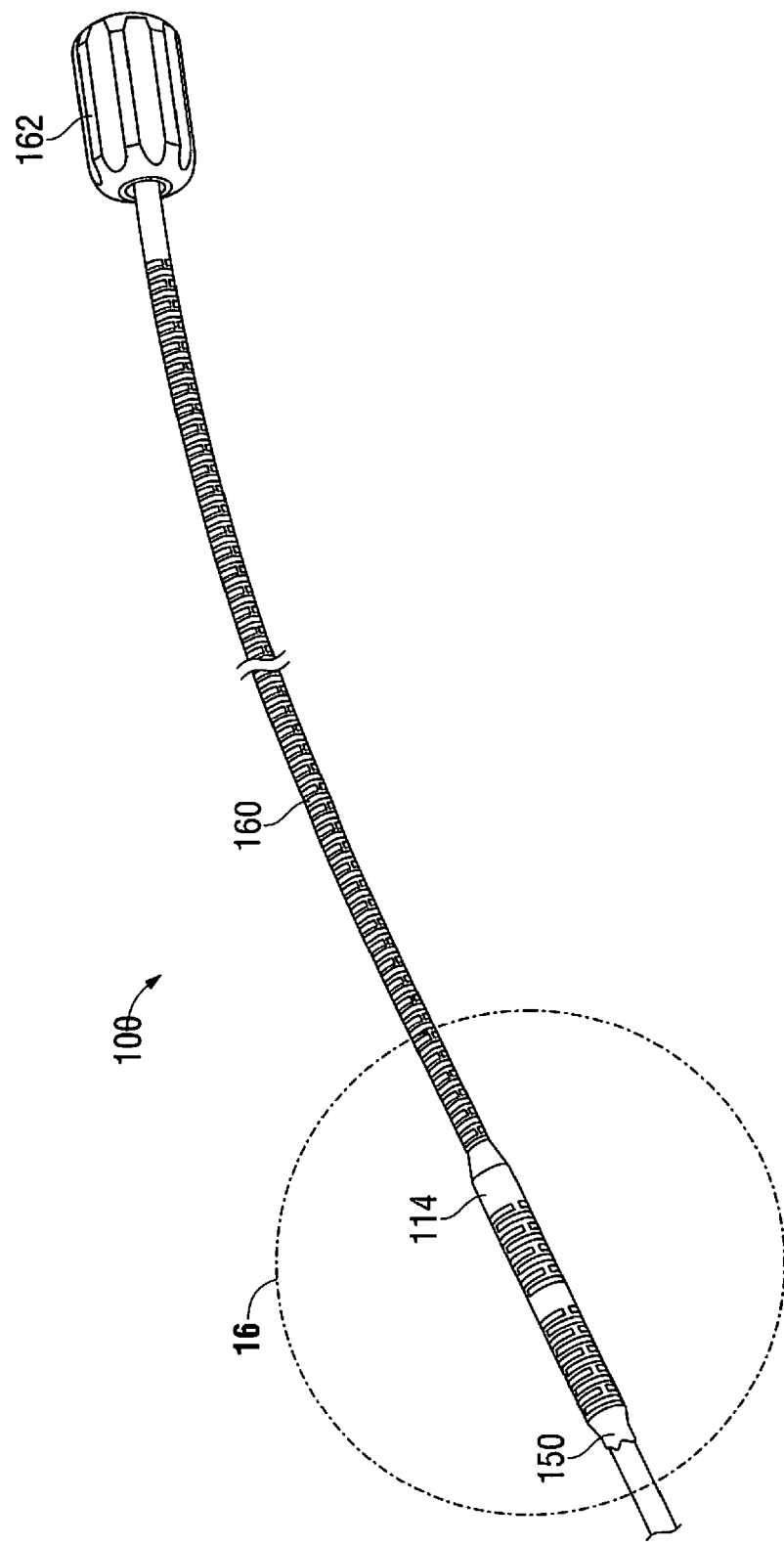
FIG. 15 is a perspective view of an alternate embodiment of the lead extractor of the present disclosure having a flexible tube.
Figure 16:
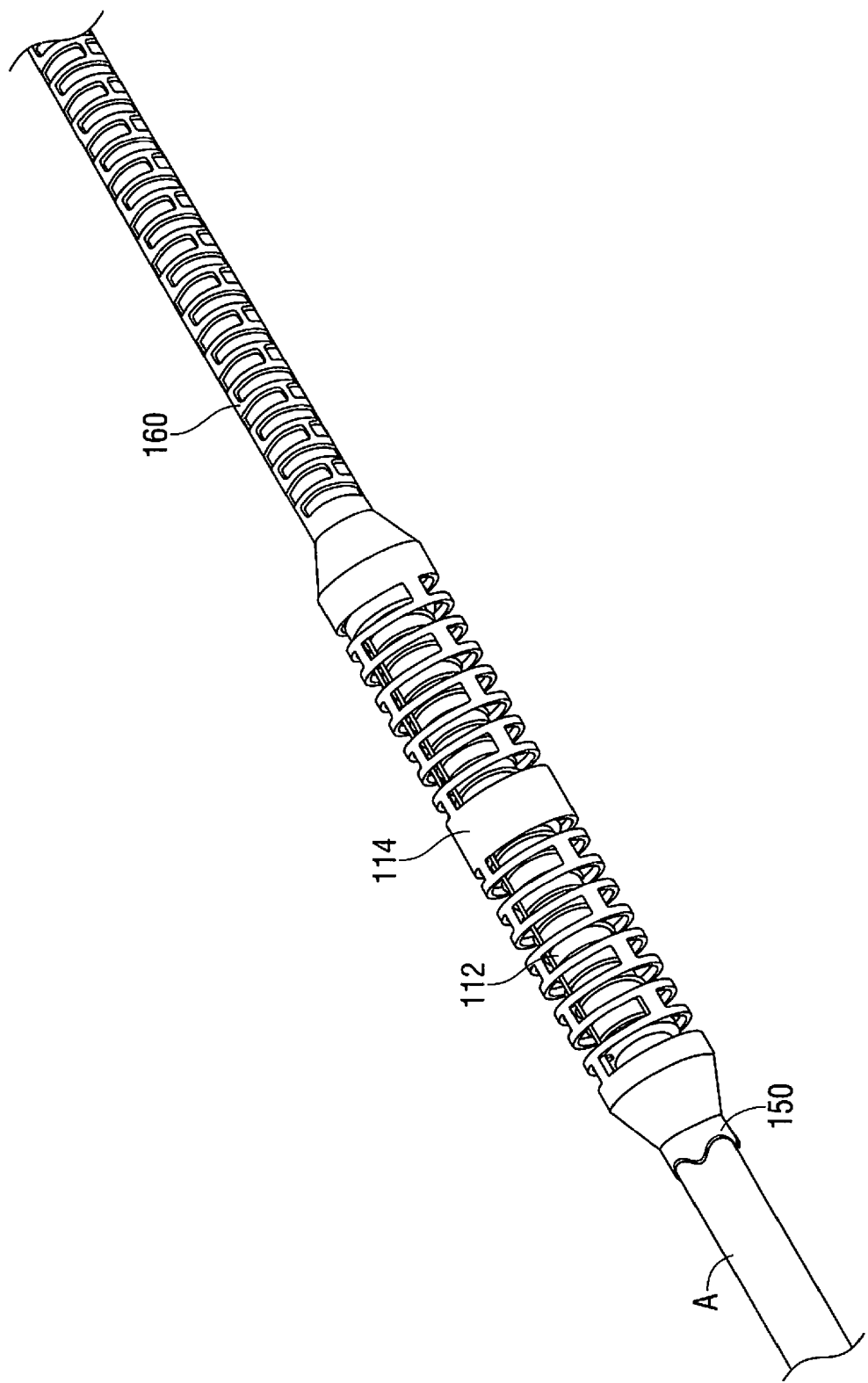
FIG. 16 is a close up perspective view of the area of detail of FIG. 15.
Figure 17:
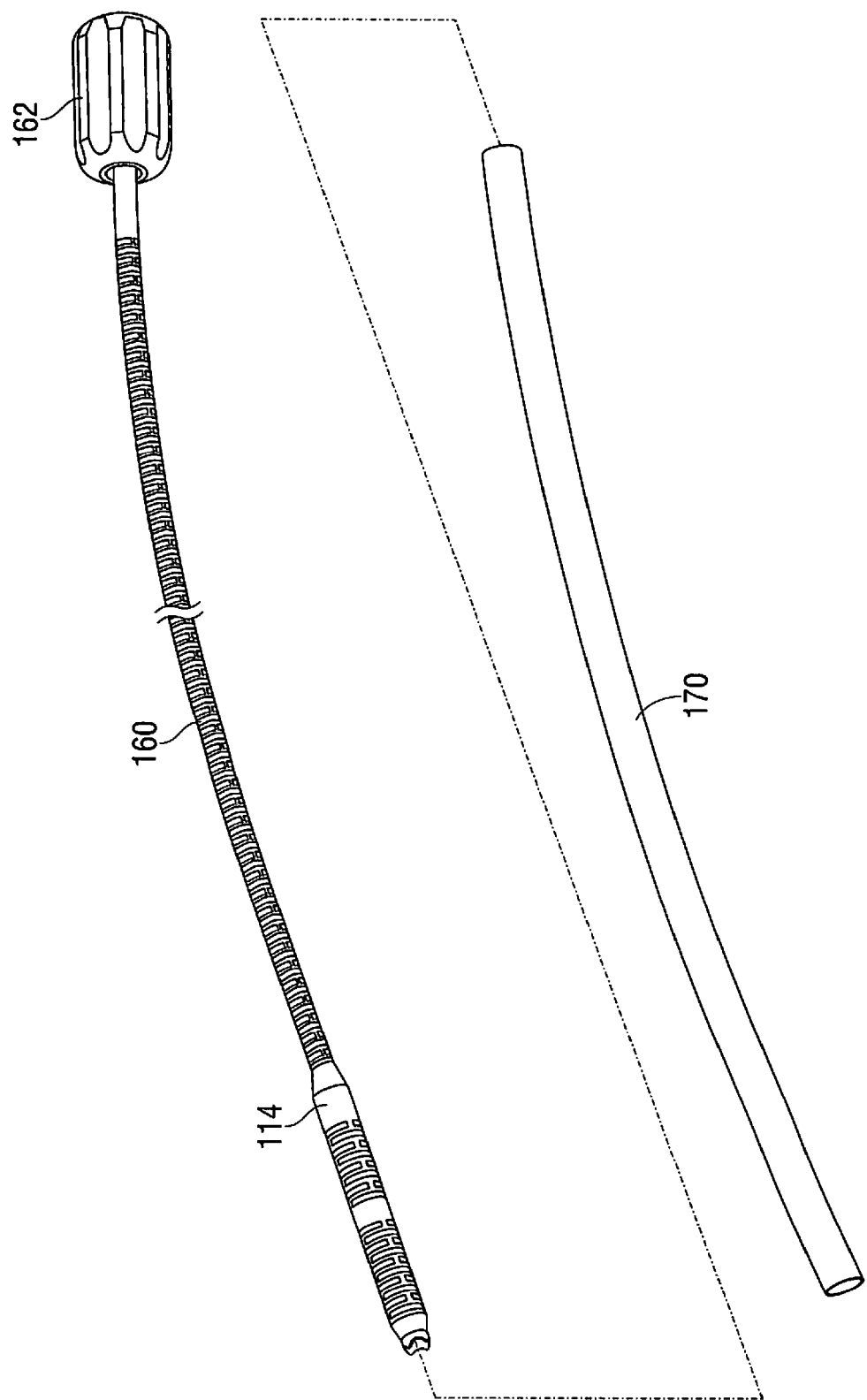
FIG. 17 illustrates a perspective view of another alternate embodiment of the lead extractor.
Figure 18A:
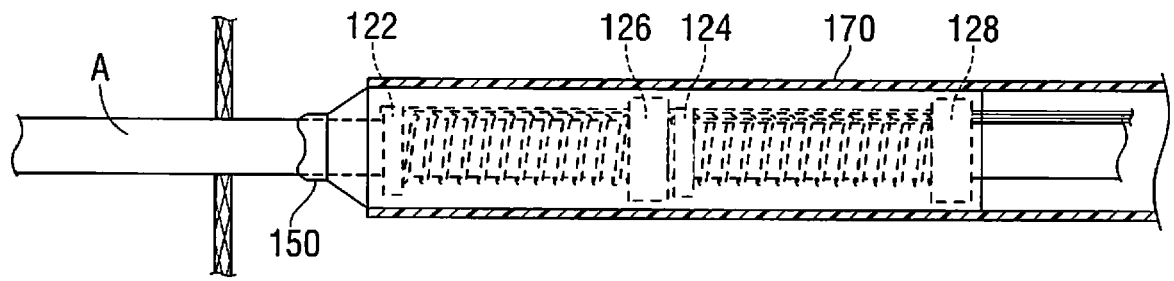
Figure 18B:
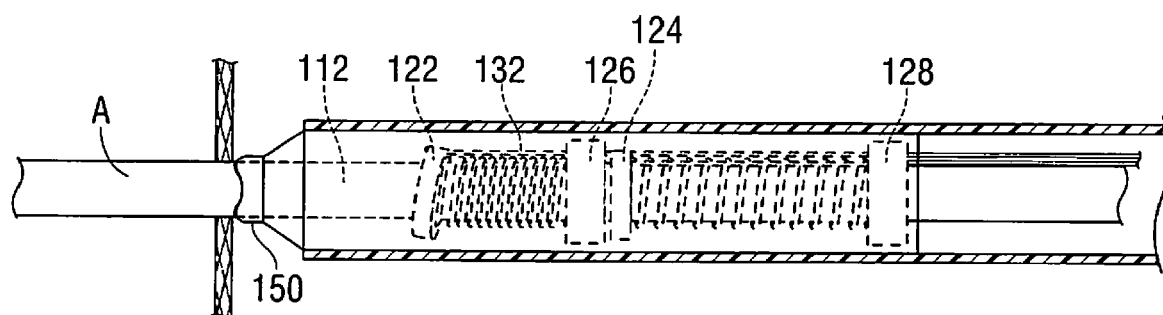
Figure 18C:
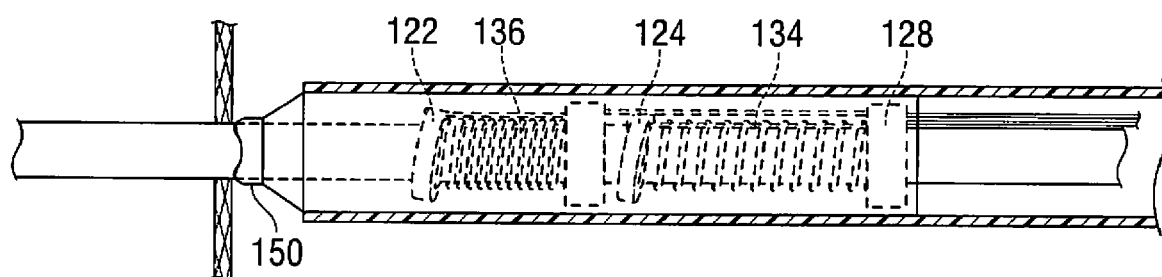
Figure 18D:
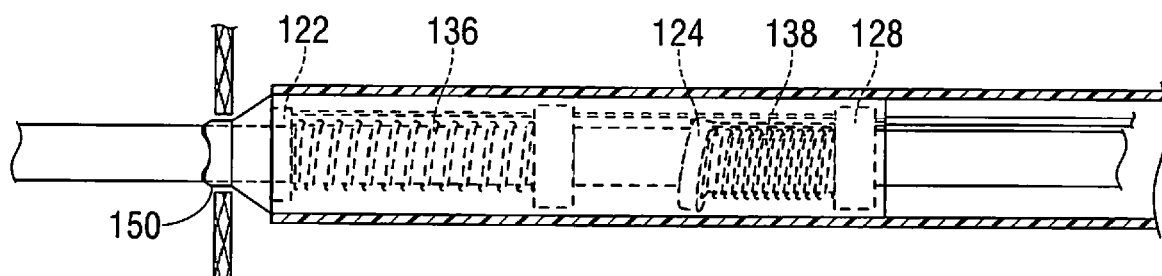

In one embodiment, this alternating movement can be achieved by handle mechanism 80 shown in FIG. 14. The handle mechanism 80 includes a first actuator 82, illustratively in the form of a pivotable handle with a finger loop 83, and a second actuator 84, also illustratively in the form of a pivotable handle with a finger loop 85. The first actuator 82 is operatively connected to the first cable 32 such that proximal movement of the actuator 82, e.g., moving of the finger loop 83 toward stationary handle 86, pulls the cable 32 proximally and distal movement returns the cable 32 to its original position. Similarly, second actuator 84 is operatively connected to the second cable 34 such that proximal movement of the actuator 84 (away from the stationary handle 86) pulls the cable 34 proximally and distal movement returns the cable 34 to its original position. The handle mechanism 80 in a preferred embodiment includes a locking mechanism (not shown) to ensure that either cable 32, 34 cannot be released until the other cable has been moved proximally to move its respective clamping ring to the angled clamping position to frictionally engage the lead. A rotation knob 88 can be provided to rotate the lead extractor to thereby rotate the clamped lead if desired.

As can be appreciated, the pistol grip and pivotable handles are shown by way of example as other handle configurations and other types of actuators, e.g., sliding tabs, are also contemplated to provide manual control of the cable movement.

Figure 11A:
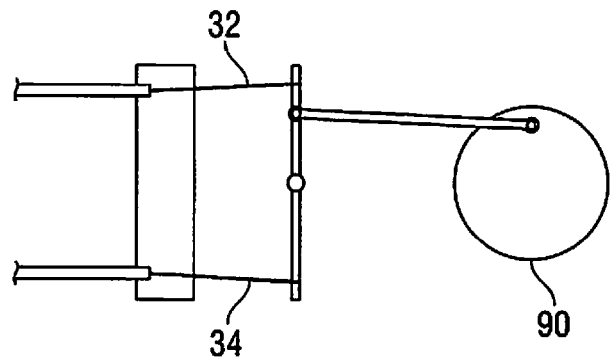
FIGS. 11A-11C are schematic views of an embodiment utilizing a motor to move (oscillate) the cables of the lead extractor to alternatively angle and retract the distal and proximal clamping rings.
Figure 11B:
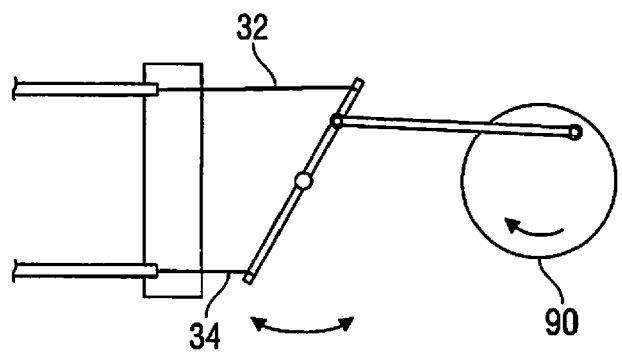
Figure 11C:
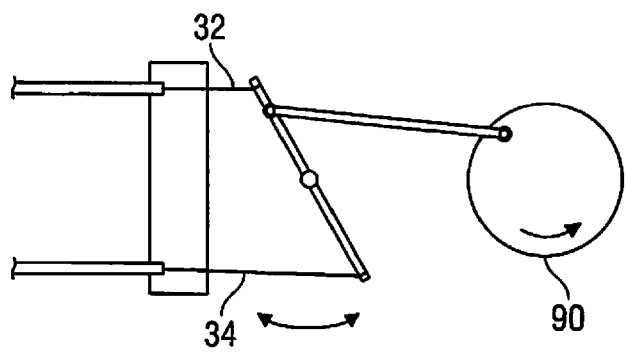

In an alternate embodiment, an external power source such as a motor assembly is provided to electrically drive (actuate) the cables instead of the manual operation by the user. As shown schematically in FIG. 11A, motor rotation of the wheel 90, which is preferably eccentric, from the neutral position of FIG. 11A to the position of FIG. 11B, pulls cable 32 proximally to move the distal clamping ring 22 to the angled position and then to pull the distal clamping ring 22 proximally to retract or swallow the clamped lead as described above. Rotation of the wheel in the opposite direction (FIG. 11C) will cause cable 34 to be pulled proximally to move the proximal clamping ring 24 to the angled position and to pull the proximal clamping ring 24 proximally to retract the clamped lead further proximally or further swallow lead. Thus, as can be appreciated, the motor causes the oscillating motion of the wheel and respective cables to incrementally relatively retract the lead. It should be appreciated that the motor controlled embodiment can be configured so that the clamping ring cannot be released from its angled position until the other clamping ring is moved to its angled clamping position as described above. Note that such motor operated cables can be utilized with the other embodiments disclosed herein, e.g., extractor 200 discussed below.

FIGS. 15-18 illustrate an alternate embodiment of the lead extractor, designated generally by reference numeral 100. The lead extractor 100 is identical to the lead extractor 10 of FIG. 2 except for provision of the flexible tube/sheath. Therefore, the identical components have been labeled with corresponding numbers in the "100 series" so that extractor 100 has a knife (cutter) 150, distal clamping ring 122, a proximal clamping ring 124, a distal fixed ring 126, a proximal fixed ring 128, a first cable 132 operably connected to the distal clamp ring 122 and a second cable 134 operably connected to the proximal clamp ring 124. The cable 132 is operable to pivot distal clamping ring 122 from a substantially perpendicular position to an angled position and the cable 134 is operable to pivot proximal clamping ring 124 from a substantially perpendicular position to an angled position. As in the embodiment of FIG. 2, a distal spring 136 is positioned around tubular member 112 to bias the distal clamping ring 122 in a distal direction and a proximal spring 138 is positioned around tubular member 112 to bias the proximal clamping ring 34 in the distal direction.

The extractor 100 differs from extractor 10 in that a flexible tube (sheath) 160 having a handle 162 is provided. The handle 162 enables the extractor 100 to be rotated to thereby rotate the clamped lead. Such rotation provides an unscrewing action of the lead if the user deems it desirable. Thus, after the extractor 100 cuts the tissue surrounding the lead, the user can keep the extractor 100 locked to hold the lead, and the sheath can be rotated to facilitate removal of the embedded screwed-in tip of the lead. Note the tube 160 has a plurality of cutouts in the wall to provide the desired flexibility. The housing 114 can also have a plurality of cutouts in the wall to provide the desired flexibility. In the alternate embodiment of FIG. 17, a sheath 170 is provided to cover the flexible tube 160.

FIGS. 18A-18D illustrate the use of extractor 100 which is identical to the use described in conjunction with FIGS. 13A-13D except for provision of a flexible sheath 170 in which the housing 114 is positioned. Thus, as can be appreciated the movement of the clamping rings 122 and 124, and relative movement of the extractor 10 and the lead A shown in FIGS. 18A-18D are identical to that of FIGS. 13A-13D and for brevity are not repeated herein.

Although two clamping rings are described in the embodiments herein, it is also contemplated that a single clamping ring or more than one clamping ring can be utilized.

Figure 19:
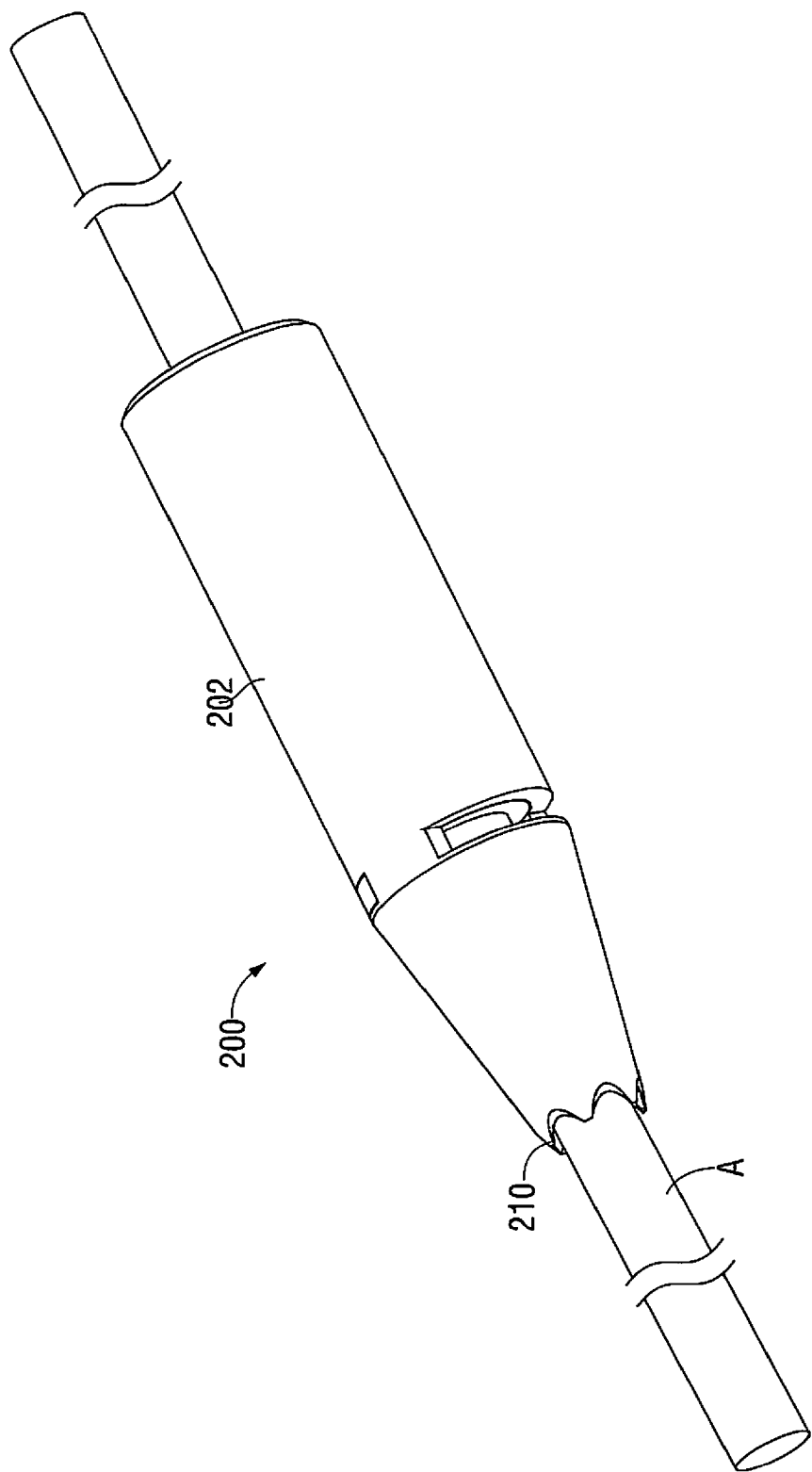
FIG. 19 is a perspective view of an alternate embodiment of the lead extractor of the present disclosure shown positioned over a cardiac lead.
Figure 20:
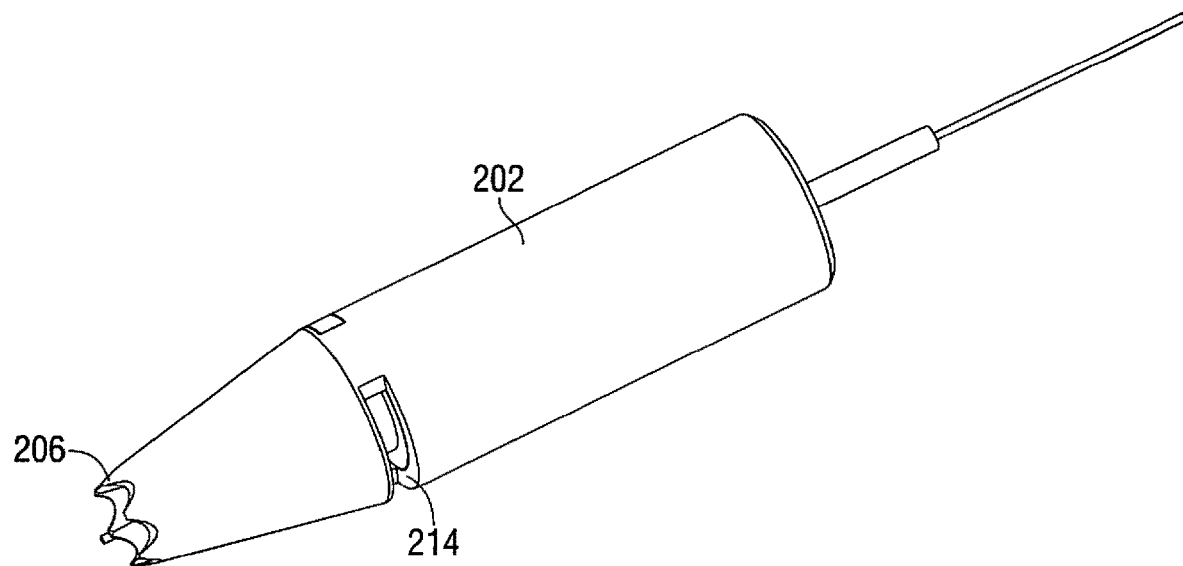
FIG. 20 is a perspective view of the outer housing of the lead extractor of FIG. 19.

An alternate embodiment of the lead extractor of the present invention is illustrated in FIGS. 19-36. The lead extractor is designated generally by reference numeral 200 and includes an outer body (outer housing) 202 and an inner body (inner housing) 204. The lead extractor 200 is similar to lead extractor 10 described above in that it is configured to move relative to the lead to "swallow" the lead in increments. However, in the lead extractor 10 of FIG. 2, the user manipulates the actuators to selectively control pivoting of the clamping members, alternately clamping and releasing the distal and proximal clamping members. In the lead extractor 200 of FIG. 19, the changed orientation of the clamping members is a result of the relative movement of the lead extractor 200 and lead. Additionally, the lead extractor 200 has an enhanced cutting action as the cutter also rotates. Other differences between extractor 200 and extractor 10 will become apparent from the detailed description below of extractor 200.

Turning to the components of lead extractor 200, and with reference to FIGS. 20-24, outer body (or outer tube) 202 of lead extractor 200 has a proximal portion 206, a distal portion 208 and an intermediate portion 207 therebetween. A cutter or cutting portion 210 is formed at the distal portion 208 and preferably includes a serrated edge or toothed edge to effectively cut tissue adjacent the lead. Outer body 202 is positioned coaxially over inner housing (or inner tube) 204 as the inner housing 204 is received in lumen 216 of outer body 202. Outer body 202 has an internal helical slot 218 and is rotatable relative to inner housing 204 (see FIGS. 35 and 36) to cut (sever and/or dissect) tissue as described in more detail below. Outer housing 202 has a conical tip 202a tapering in a distal direction to facilitate tunneling of the device. Radial slots 212, 214 receive disc 231 and another disc (not shown) or bars which are welded to the outer tube 202 to keep the device 200 together. Also, these block axial movement of the outer body 202 so that when the carrier 240 moves axially, since axial movement of the outer body 202 is blocked, it is forced to rotate.

Figure 21:
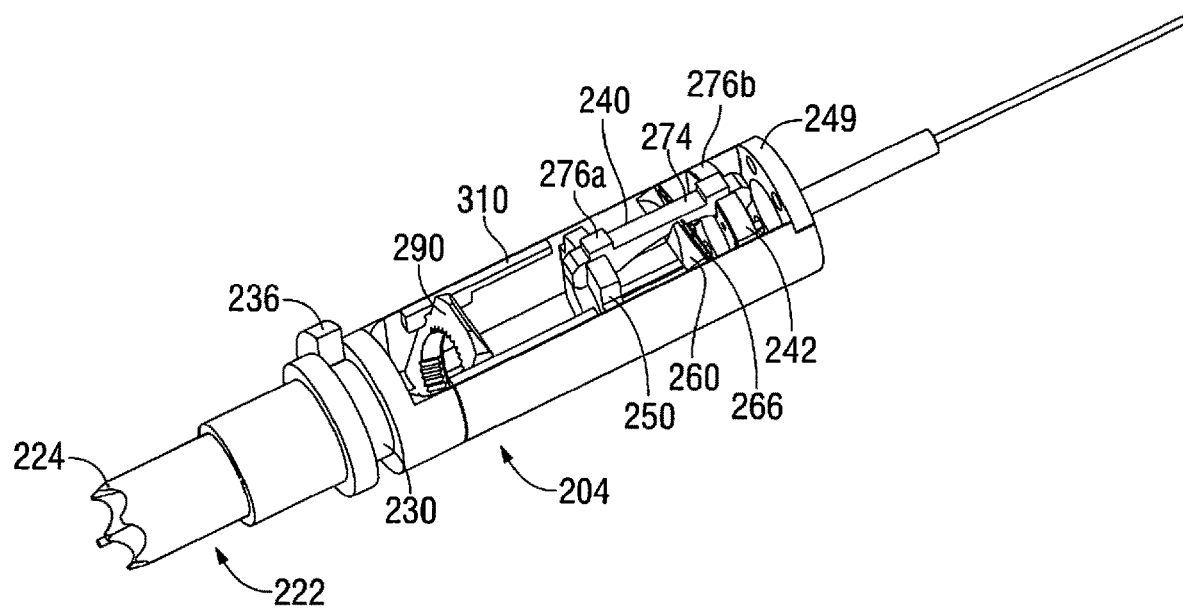
FIG. 21 is a perspective view of the inner housing of the lead extractor of FIG. 19.
Figure 22:
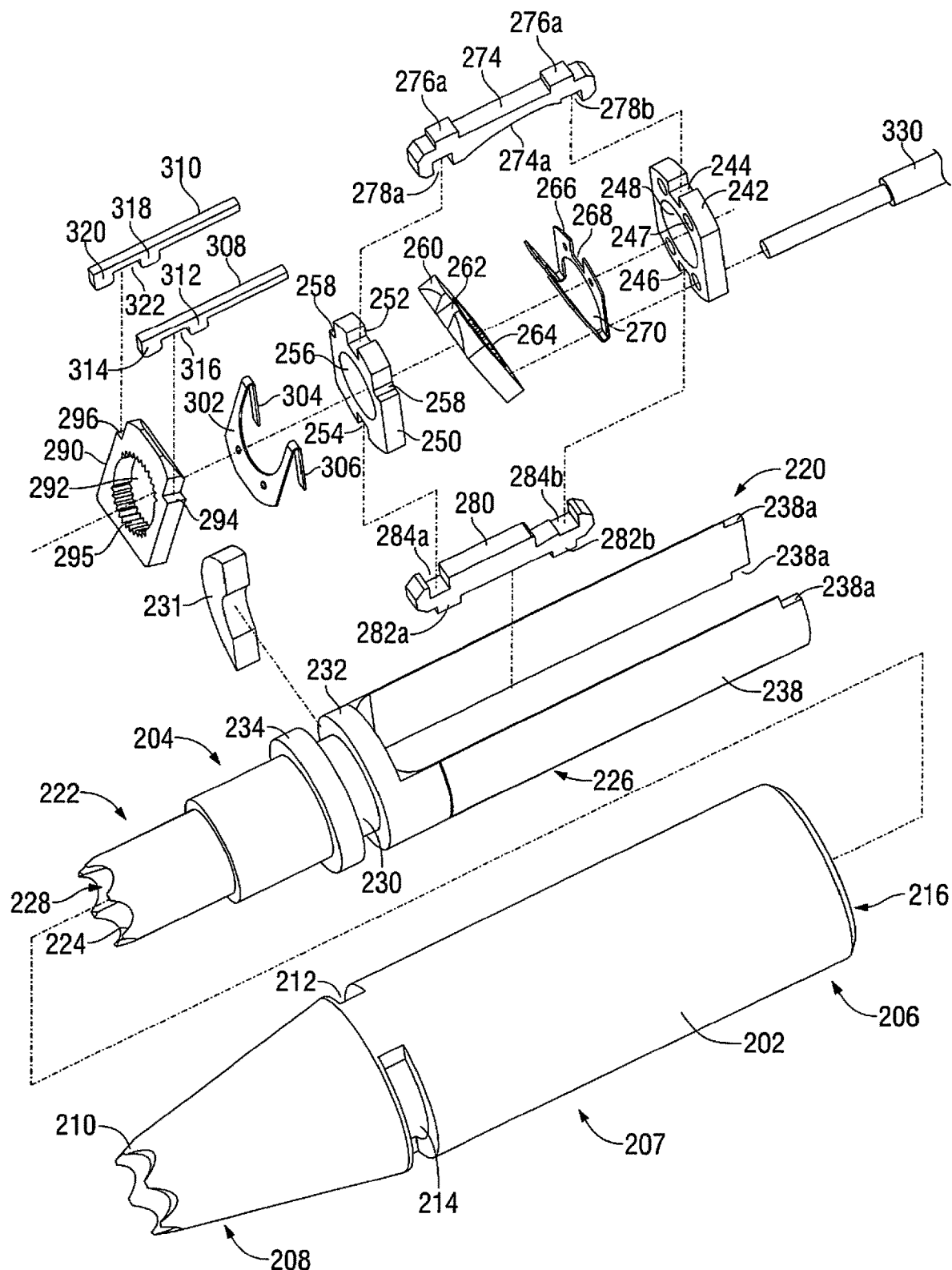
FIG. 22 is an exploded perspective view of the lead extractor of FIG. 19.
Figure 23:
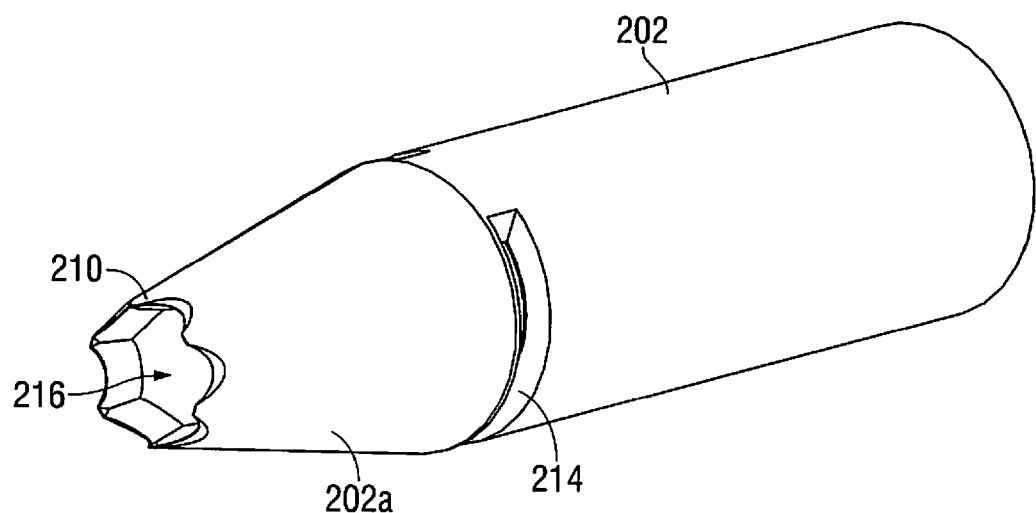
FIG. 23 is a perspective view of the outer housing of the lead extractor of FIG. 19.
Figure 24:
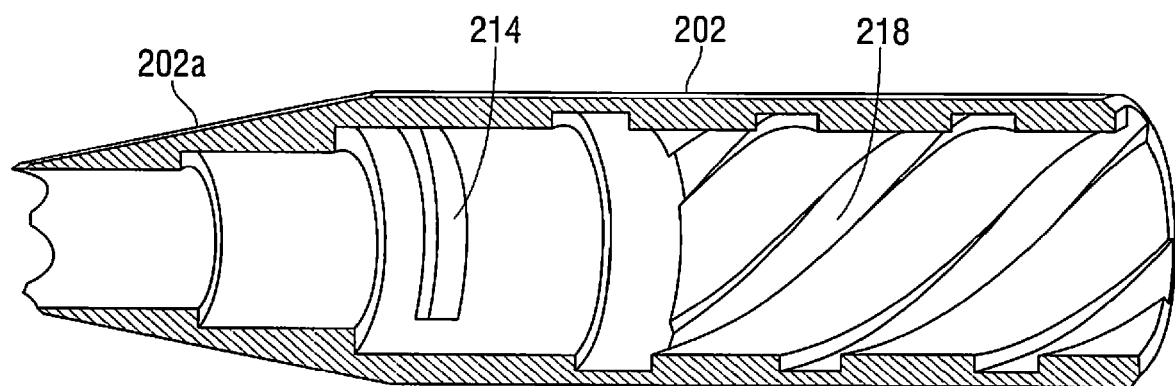
FIG. 24 is a cross-sectional view of the outer housing of FIG. 23.

With reference to FIGS. 21-22, the inner housing 204 has a proximal portion 220, a distal portion 222 and an intermediate portion 226 between the proximal portion 220 and distal portion 222. A cutter or cutting portion 224, preferably having a serrated or toothed edge as shown, interacts with the cutting portion 210 of outer housing 202 to sever tissue adjacent the lead. That is, the cutting portion 210 of outer housing 202 overlies a counterpart cutting portion 224 of inner housing 204. A circumferential slot 230 is formed between ring 234 and distal end 232 of the carrier receiving portion to receive semicircular disc 231.

Inner housing 204 has a pair of proximally extending arms 238 to form a gap to slidably receive carrier or vehicle 240. Movement of carrier 240 effects relative movement of the extractor 200 and lead. A proximal end cap 249 is secured within top and bottom notches 238a of arms 238 to secure the arms 238 and provide a back wall enclosure for the inner housing 204. Carrier 240 is slidably mounted within inner housing 204 for movement between proximal (retracted) and distal positions, proximal defined as noted above as the region closer to the user and distal as the region further from the user (and closer to the tip of the lead). The movement of carrier 240 provides the desired clamping of the lead which is positioned within the lumen 228 of inner housing 204. A cable 330 described in detail below effects movement of the carrier 240.

Figure 25:
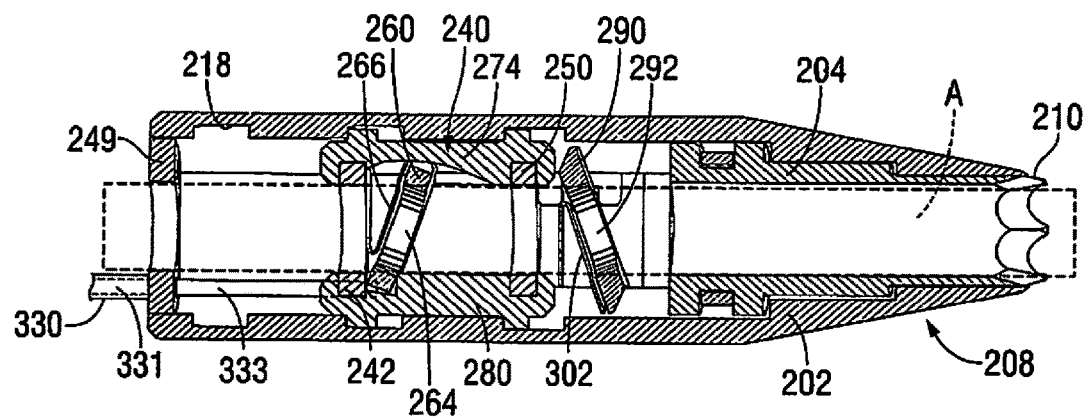
FIG. 25 is a cross-sectional view illustrating the lead extractor in the initial position and showing the lead extending through the extractor.
Figure 26:
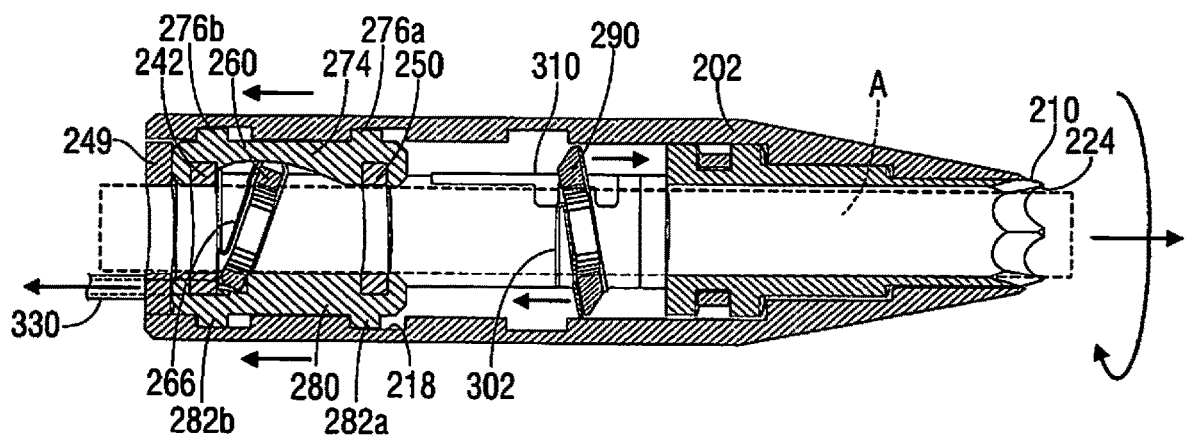
FIG. 26 is a cross-sectional view similar to FIG. 25 illustrating the carrier of the lead extractor moved to the proximal position.

Carrier 240 is formed by proximal fixed support ring 242, distal fixed support ring 250, upper support 274 and lower support 280. The terms "upper" and "lower" as used herein refer to the orientation of the device in the orientation shown in the drawings and are used herein for ease of description. Clearly, if the orientation of the device changes, the references "upper" and "lower" will also accordingly change. Contained within carrier 240 is proximal clamping ring 260 which has a hinge point on its lower surface and is biased by proximal spring 266 to a tilted position (with respect to the longitudinal axis of the extractor 200 and lead) as shown in FIGS. 21 and 25. In this tilted position (tilted toward the distal end of the device), the proximal clamping ring 260 provides a clamping force on the lead as its central opening 264 is sufficiently angled with respect to the outer surface of the lead so the surface surrounding opening 264 grasps (clamps) the lead. Upper support 274 has a distal notch 278a seated within upper notch 252 of distal fixed support ring 250 and a proximal notch 278b seated within upper notch 244 of proximal fixed support ring 242 to retain and secure these components. Similarly, lower support 280 has a distal notch 284a seated within lower notch 254 of distal fixed support ring 250 and a proximal notch 284b seated within lower notch 246 of proximal fixed support ring 242 to retain and secure these components. Upper tabs 276a, 276b of upper support 274 and lower tabs 282a, 282b of lower support 280 interact with the helical slot 218 formed in the outer housing 202 described in more detail below. Proximal clamping ring 260 receives elongated portion 274a of upper support 274 in upper slot 262. A similar slot on the opposing (bottom) side of proximal clamping ring 260 receives lower support 280. A slot 268 of proximal spring 266 accommodates upper support 274. Spring 266 is hinged at a bottom portion and has an opening 270 through which the lead can extend. Spring 266 is preferably attached to proximal clamping ring 260.

Distal of carrier 240, positioned within inner housing 202 between arms 238, is a distal clamping ring 290 which has a hinge point on the top surface and is biased by distal spring 302 to the tilted position as shown in FIGS. 21 and 25. Spring 302 is preferably attached to distal clamping ring 290 and hinged at a top portion. As can be appreciated, the distal clamping ring 290 and proximal clamping ring 260 have hinge points on opposing sides of the longitudinal axis of the device 10. In the tilted position of FIG. 21, (tilted toward the proximal end of the device), the distal clamping ring opening 290 is at a sufficient angle with respect to the lead such that the lead is clamped by the ring 290. A ridged, toothed or irregular surface 295 is formed around part or alternatively the entire circumference of opening 292 in distal clamping ring 290 to enhance clamping of the lead extending therethrough when the distal clamping ring 290 is in the tilted position. Such ridged, toothed or irregular surface can also be provided around part or the entire circumference of the opening 264 of proximal clamping ring 260 to enhance clamping of the lead.

Clamp engaging member 308 has a distal tab 314 and proximal tab 312. Clamp engaging member 310 similarly has a distal tab 320 and a proximal tab 318. The clamp engaging members 308, 310 are seated within side notches 294, 296, respectively, of distal clamping ring 290. The tabs 314, 312, 318, and 320 support and retain the upper end of the distal clamping ring 290.

Cable 330 (FIG. 25) includes an outer cable 331 which is attached to the end cap 249 of inner housing 204. Coaxially positioned within the outer cable 331 is inner cable 333, which extends distally from outer cable 331 and is attached to the fixed proximal ring 242 of carrier 240. Cable 333 provides a movement mechanism as proximal movement of inner cable 333 pulls the carrier 240 in a proximal direction and distal movement of the inner cable 333 pushes the carrier 240 in a distal direction. The cable 333 is actuated by a trigger 340 shown in FIG. 41 and described in conjunction with the method of use.

The use of the extractor 200 will now be described for use to extract an implanted cardiac lead, it being understood it can be used to extract other leads or other components/devices. Oftentimes, tissue ingrowth and plaque builds around the lead over a period of time which makes extraction difficult. The extractor 200 functions to extract the lead by application of the force at the distal end. That is, the lead extractor 200 is advanced in steps (increments) relative to the lead, thereby cutting e.g., severing and/or dissecting, tissue about the lead and tunneling around the lead to cut it away from tissue. When the tissue has been cut away, the lead can be extracted from the heart tissue. The extractor 200 and lead A are relatively movable with respect to each other. Therefore, if the lead is fixed, then the extractor 200 will move progressively (in discrete increments) over the lead; if the lead is not fixed, then the extractor will progressively pull the lead (in discrete increments) back into the extractor 200. Alternatively, both the extractor and lead can move in opposing directions. In any event, this relative movement causes the "swallowing" of the lead by the extractor 200.

FIGS. 25-29 show in cross-sectional views operation of the extractor 200. FIGS. 30-34 are perspective views corresponding to the respective positions of FIGS. 24-29, however the inner housing 204 and outer housing 202 have been removed for clarity.

Figure 30:
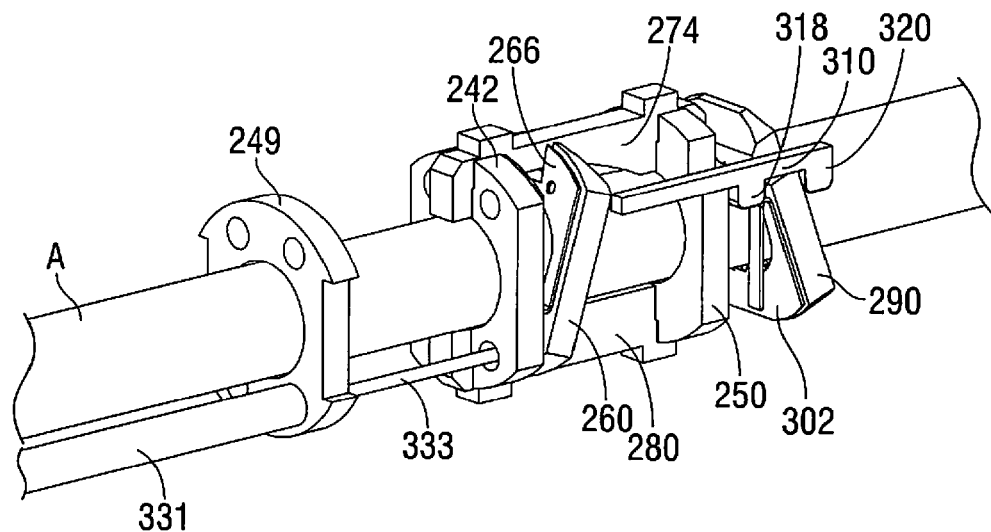
FIG. 30 is a perspective view corresponding to the position of FIG. 25, the inner and outer housings removed for clarity, and showing the lead extending through the extractor.

In use, the device 200 is inserted over a proximal end of the lead, e.g., a cardiac lead, which is embedded in tissue and desired to be removed. The extractor 200 is advanced until the distal end 208 of the outer housing 202 encounters hard tissue. Note, in the insertion position, the proximal clamping ring 260 is tilted toward the distal end and the distal clamping ring 290 is tilted toward the proximal end as shown in FIGS. 25 and 30. In this position, the extractor 200 can be forced over the lead A with the openings 292 and 264 of distal and proximal clamping rings 290, 260 providing a sufficient gap (upon such force being applied) for passage of the outer diameter of the lead and not providing a sufficient clamping or frictional force on the lead A to prevent such passage. In this initial position for insertion over the lead, springs 266 and 302 are not compressed and bias the clamping rings 260, 290, respectively in the tilted positions shown. Note the clamping rings 260, 290 can optionally be moved to a less tilted position by movement to the override position described below for initial insertion of the lead, however, in this embodiment it is not necessary since the extractor 200 can be forced over the lead.

Figure 31:
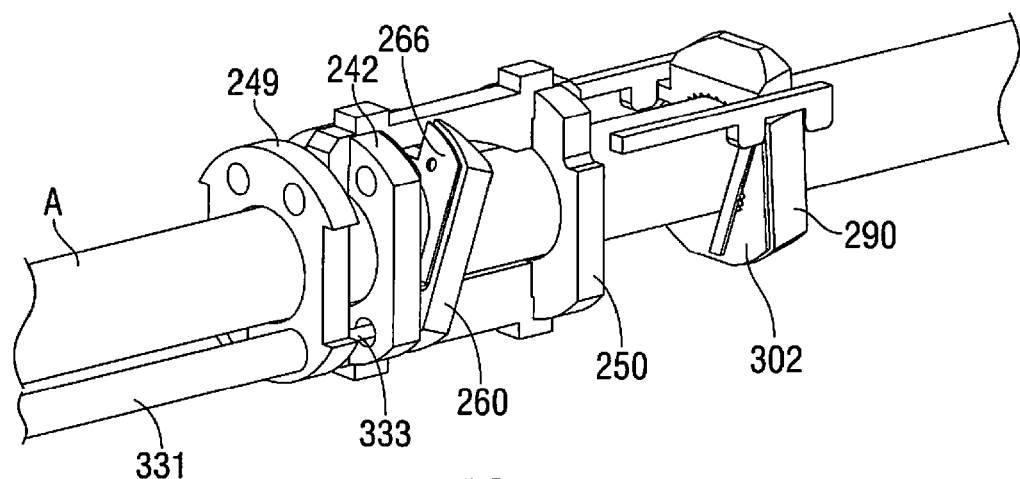
FIG. 31 is a perspective view corresponding to the position of FIG. 26, the inner and outer housings removed for clarity.
Figure 32:
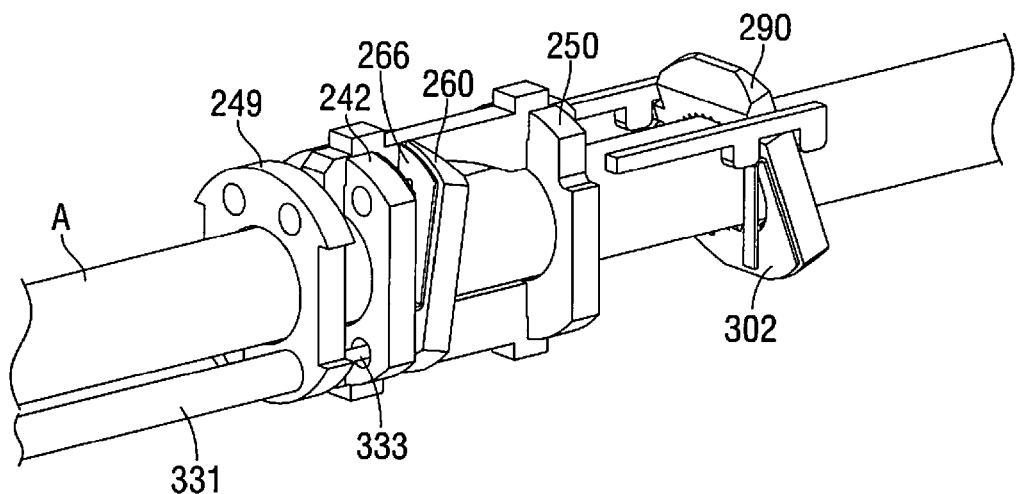
FIG. 32 is a perspective view corresponding to the position of FIG. 27, the inner and outer housings removed for clarity.
Figure 33:
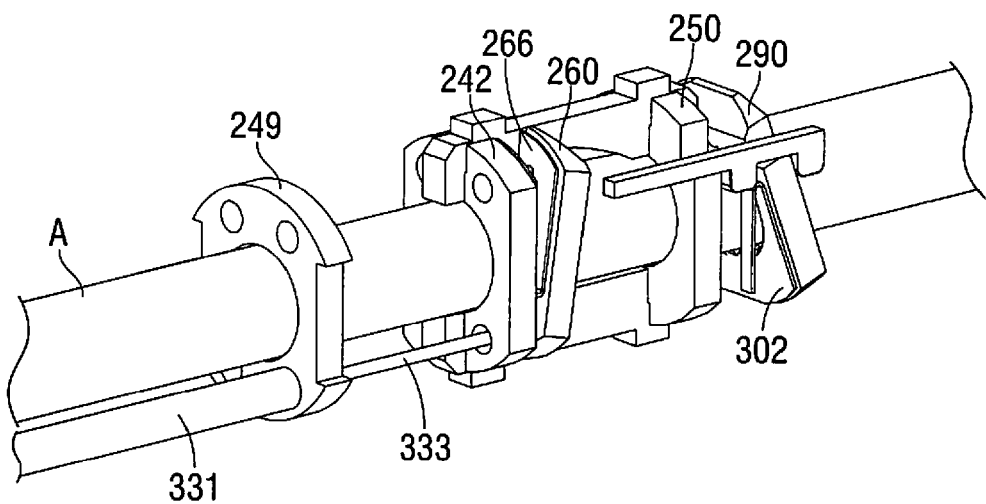
FIG. 33 is a perspective view corresponding to the position of FIG. 28, the inner and outer housings removed for clarity.

When hard tissue, e.g., plaque, is encountered so that the extractor 200 cannot be further advanced sufficiently easy over the lead, the user actuates trigger 340 (FIG. 42) to thereby pull inner cable 333 proximally, which pulls the carrier 240 proximally since cable 331 is attached to the fixed proximal ring 242. When the carrier 240 is pulled back, shown by the proximally pointing arrows of FIG. 26, the extractor 200 is advanced distally over the lead A as proximal clamping ring 260 clamps lead A. Note the more relative movement of carrier 240 and lead A, the more tilting of the proximal clamping ring 260 and more clamping force applied to the lead A. Simultaneous with such proximal movement of the carrier, the outer housing 202 rotates, preferably about 45 degrees although other degrees of rotation are also contemplated, due to the engagement of tabs 276a, 276b (of upper support 274) and the engagement of tabs 282a, 282b (of lower support 280) with the internal helical slot 218 of outer housing 202. This axial and rotational movement of outer housing 202, in cooperation with the stationary (non-rotating) cutting portion 224 of inner housing 204, facilitates the cutting portions cutting through tissue around the lead A. This retracted position of carrier 240 is also shown in FIG. 31. Note as the carrier 240 is retracted, distal clamp ring 290 is pivoted about upper hinge point in a clockwise direction, compressing spring 302. The relative movement of the extractor 200 and lead A causes the distal clamping ring 290 to move to this less angled position of FIG. 26 to facilitate movement of the extractor 200 as the opening in the distal clamping ring 290 provides a larger diameter with respect to the outer diameter of the lead A and no longer provides a restrictive clamping force on the lead A. Although the angle of the proximal clamping member 260 might not substantially change during such retraction of carrier 240, remaining in substantially the same position as in FIG. 25, biased by spring 266, it will tilt more if needed such as if a larger force is applied.

Figure 27:
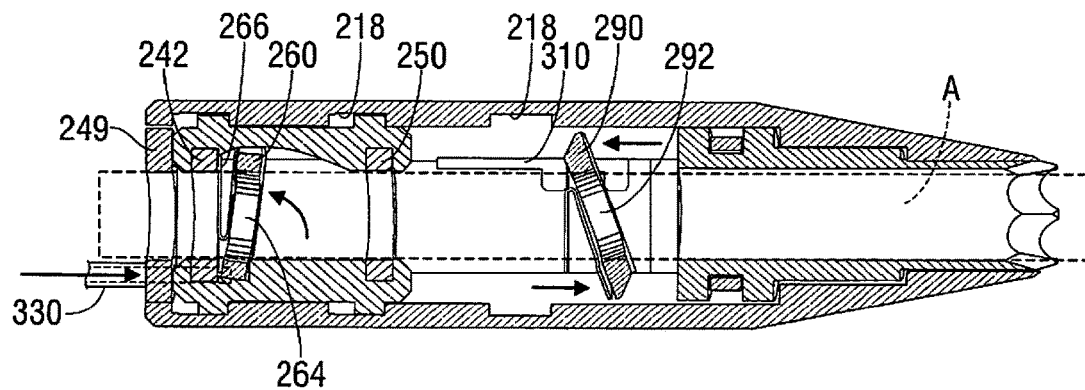
FIG. 27 is a cross-sectional view similar to FIG. 26 illustrating the carrier of the lead extractor starting to be returned to the initial distal position.
Figure 28:
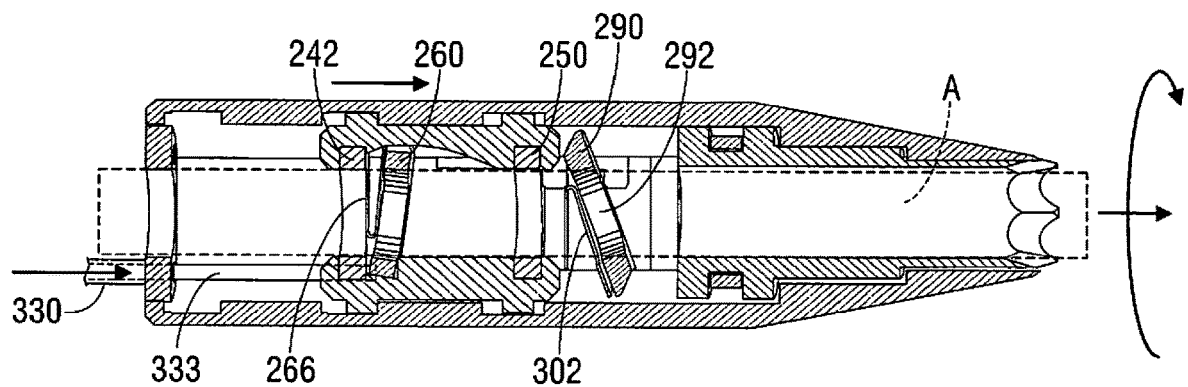
FIG. 28 is a cross-sectional view similar to FIG. 27 illustrating the carrier of the lead extractor moved to the distal position.

Next, the trigger 252 is returned to the neutral position (FIG. 41), thereby pushing cable 331 distally, which pushes the carrier 240 distally in the direction of the arrow of FIG. 27 to reset the extractor 200 for the next incremental movement. As shown in FIGS. 27 and 31, in the initial movement of the carrier 240 distally, the interaction with the lead A pivots the proximal clamping ring 260 about its bottom hinge in a counterclockwise direction to a more vertical position, thereby compressing spring 266, and creating a larger diameter gap about opening 264 with respect to the outer diameter of the lead A to facilitate movement of the extractor 200 with respect to the lead A. The carrier 240 thereby moves to the distal position of FIGS. 28 and 33, with proximal clamping ring 260 remaining in the less tilted (and unclamped) position as a result of such movement. Distal clamping member 290 returns to the tilted position of FIG. 25 as the extractor 200 is moved relative to lead A and it remains in the tilted clamping position to clamp the lead A and prevent the lead shifting back, i.e., reversing itself. Such distal movement of carrier 240 causes the outer housing 202 to rotate during its axial advancement due to the tab/helical slot 218 engagement discussed above, the axial movement and rotation of the cutter (rotating relative to the fixed cutting portion of inner housing 204) cutting tissue around the lead A. Note the clamping member 290 prevents the lead from moving back and there is no (or little) relative movement of the lead and extractor 200. However, the outer housing 202 will still rotate upon movement of the carrier 240, thus making the same but opposite cutting movement when the carrier 240 is moved distally.

Figure 29:
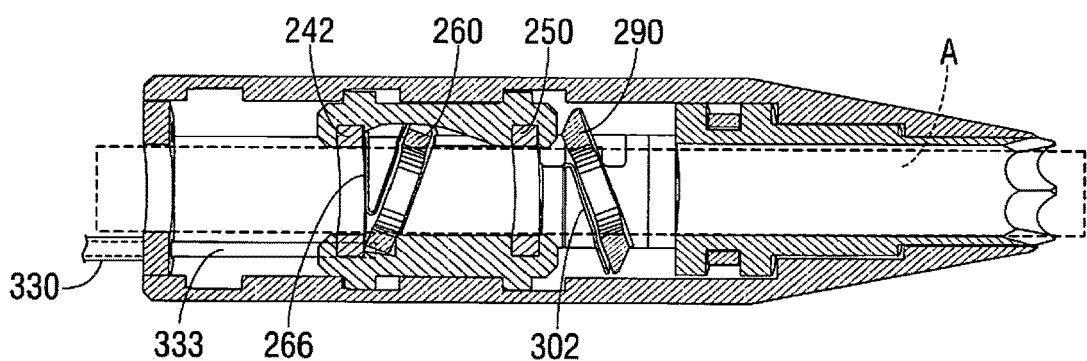
FIG. 29 is a cross-sectional view similar to FIG. 28 illustrating the carrier and components of the lead extractor in the initial position.
Figure 34:
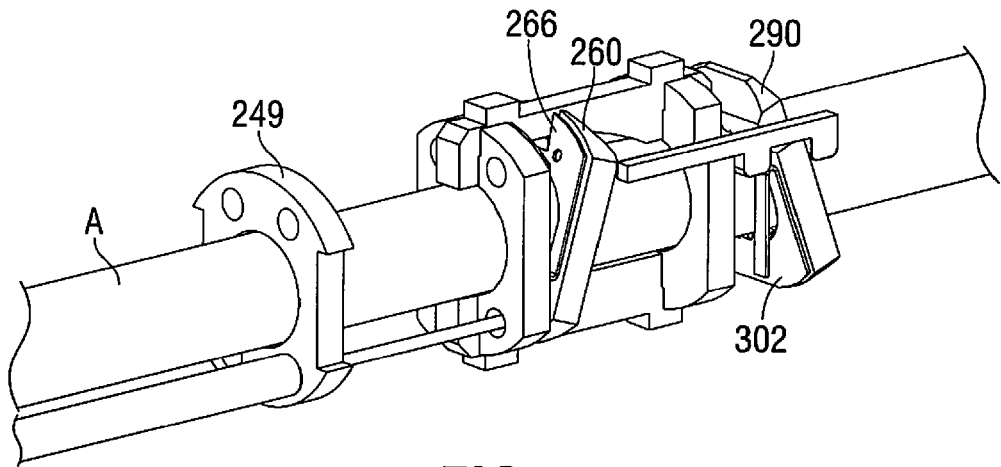
FIG. 34 is a perspective view corresponding to the position of FIG. 29, the inner and outer housings removed for clarity.
Figure 35:
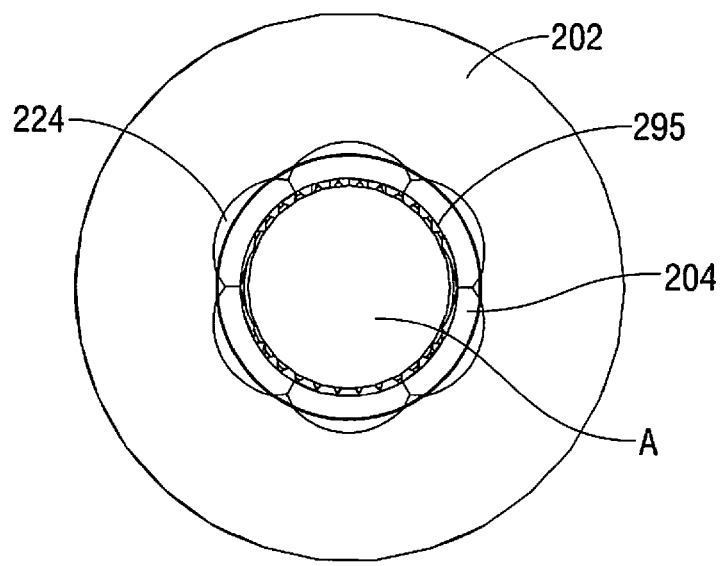
FIG. 35 is a front view of the lead extractor of FIG. 19.
Figure 36:
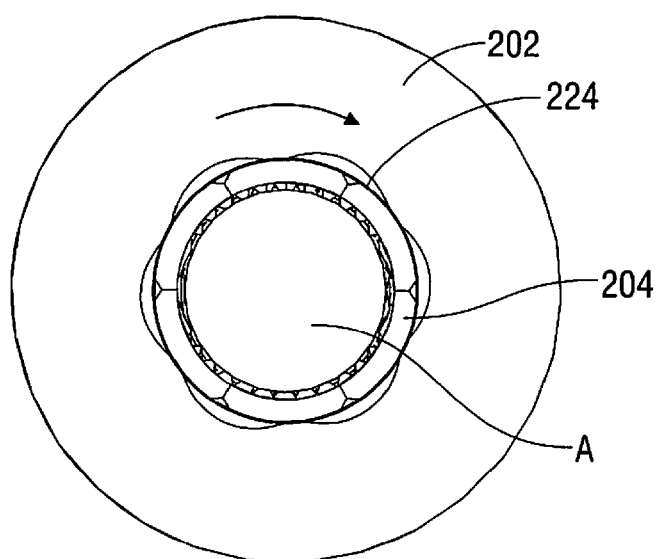
FIG. 36 is a front view similar to FIG. 35 showing rotation of the outer housing with respect to the inner housing for cutting tissue.
Figure 37:
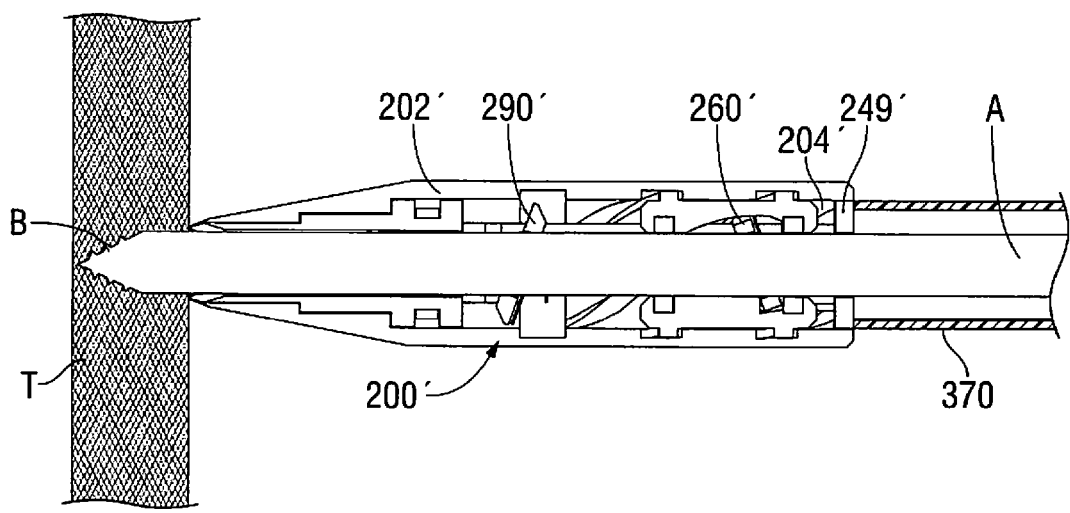
FIG. 37 is a side view of an alternate embodiment of the lead extractor of the present disclosure having a flexible sheath thereover, the sheath shown in cross-section.
Figure 38:
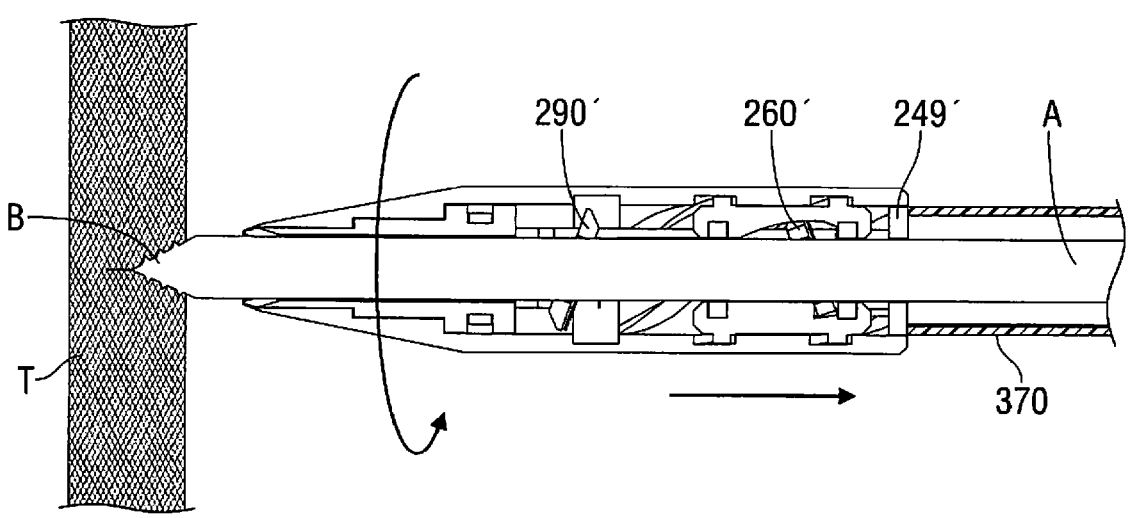
FIG. 38 is a side view similar to FIG. 37 showing rotation of the flexible sheath to rotate the extractor and lead.

After full distal travel of the carrier 240 with respect to the lead A, the carrier 240 returns to the position of FIGS. 29 and 34, which is the same position of FIGS. 25 and 30. Note that the relative movement of the extractor 200 and the lead A causes automatic tilting of the clamping rings 260 and 290. That is, due to the angular positioning of the clamping rings 290, 260, and the top and bottom hinge points, they operate as follows: when the carrier 240 is moved proximally to swallow the lead A, proximal clamping ring 290 remains in the same angular position (although it is moved axially) and distal clamping ring 290 is rotated by the lead to a less angled position; and when the carrier 240 is moved distally to reset, the distal clamping ring 290 returns, due to the lead (and assisted by spring 302), to the tilted (angular) position to prevent reverse relative movement with the lead and the proximal clamping ring 260 is tilted by the lead A to a less angled (move vertical) position. Such rotation or tilting of proximal clamping ring 260 compresses the biasing spring 266.

Note that the proximal and distal clamping rings 260, 290 do not perform a clamping function when they are not sufficiently tilted, i.e., when they are in a substantially vertical position. The springs 266, 302 aid the clamping rings 260, 290 in making the initial tilting to a more angled position. As soon as the clamping rings 260, 290 start locking on the lead as a result of relative axial movement, the tilting increases and the locking force increases. The greater the force, the better the locking on the lead.

The above steps of FIGS. 25-29 are then repeated the desired number of times by actuation of the trigger (actuating member) 340. As can be appreciated, the trigger or actuator 340 is repeatedly pulled and released, to cause progressive and incremental relative movement of the extractor 200 and lead A to cut, e.g., sever and/or dissect, tissue adjacent the lead and "swallow" the lead A to free the lead from the surrounding tissue so it can be removed from the body. As can also be appreciated, this movement and tunneling action of the extractor 200 results in the removal force applied at the distal end of the device, adjacent the tissue engagement of the lead.

Figure 41:
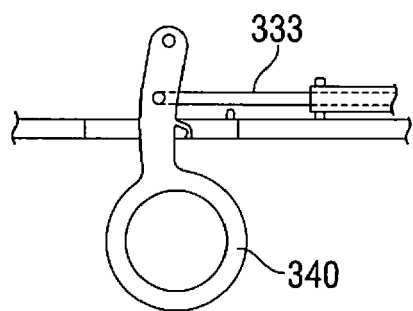
FIG. 41 is a perspective view of the actuator in a first (neutral) position.
Figure 42:
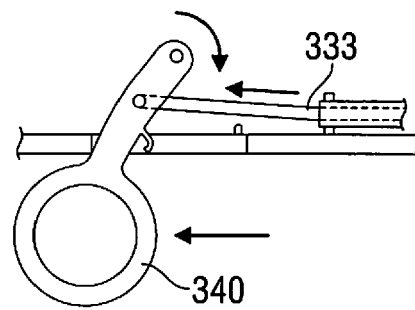
FIG. 42 is a perspective view of the actuator in a second position to pull the cable proximally to retract the carrier of the lead extractor.
Figure 43:
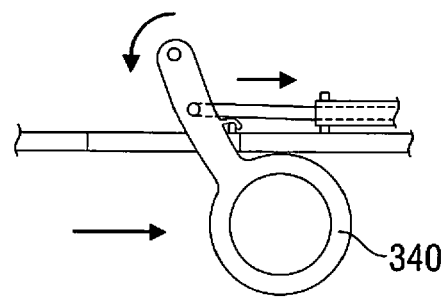
FIG. 43 is a perspective view of the actuator in an override position to advance the carrier of the electrode lead to the distal clamp release position.
Figure 44:
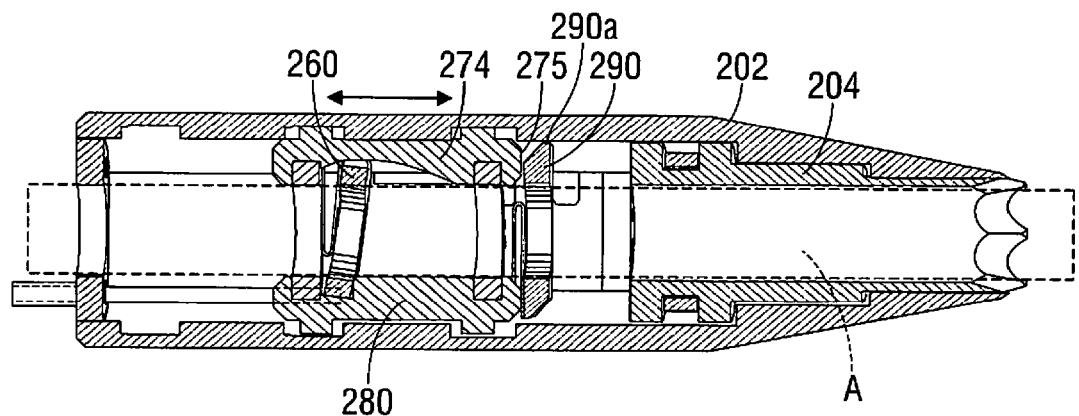
FIG. 44 is a cross-sectional view illustrating the lead extractor in the override position to release the clamping rings.

In certain instances it may be desirable to quickly abort the procedure and quickly remove the extractor 200 from the lead. This requires the clamping rings 260, 290 to be moved to the less tilted unclamping position. This is shown in FIGS. 43 and 44. FIGS. 41 and 42 show normal use of the trigger 352. As noted above, when trigger 340 is pulled back, it pulls back on cable 331 to retract the carrier 240; when trigger 340 is moved forward (distally), it pushes the carrier 240. This is the normal use of trigger 252 to achieve desired movement of the carrier and relative movement ("swallowing") of the lead. However, if during the procedure, the user desires to quickly remove the extractor 200, the trigger 340 is moved to its forwardmost (distalmost) position to move the carrier 240 to an advanced override position. This override position is distal of the carrier position of FIGS. 25 and 30. In this position, the carrier 240 is advanced so the distal edge 275 of upper support 274 contacts a proximal end 290a of distal clamping ring 290 forcing it to a less tilted position, and in some embodiments a position close to about 90 degrees with respect to the longitudinal axis of the lead A. Such movement of the carrier 240 with respect to the lead A also causes the proximal clamping ring 260 to move to the less tilted position as it does in FIGS. 27 and 28. Thus, with the less tilted position and larger gaps of the openings 292 and 264 in clamping rings 290, 260 with respect to the outer diameter of the lead, the extractor 200 can more freely slide over the lead A and be removed from the patient's body. Note a detent can be provided to limit movement of the trigger to the position of FIG. 41, and then overridden by application of sufficient force to move the trigger to the override position. Alternatively, a latch or other locking mechanism can be provided to restrict movement of the trigger to the position of FIG. 41, and released to allow movement of trigger 340 to the position of FIG. 43 to cancel the procedure. Also, a retention mechanism can be provided to retain the trigger in the override position.

Note in some embodiments the trigger 340 can be in the neutral position of FIG. 41 and then return to the position of FIG. 41 when released from the position of FIG. 42. Also, the trigger mechanism can include a stop such as a detent, which would prevent movement of the trigger 340 to the override position of FIG. 43 during its normal use, and require sufficient force of the trigger 340 to override the detent to force it into the override position of FIG. 43.

Note alternatively an external power source such as a motor can be provided to electrically drive (actuate) the cable 333 instead of manual operation by the user.

Figure 39:
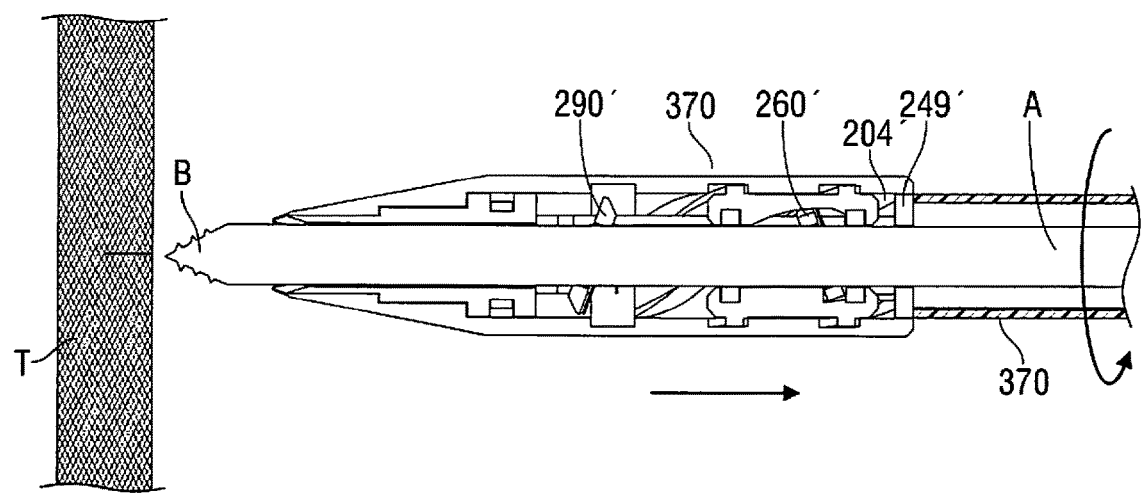
FIG. 39 is a side view similar to FIG. 38 showing freeing of the distal tip of the lead from the tissue as a result of rotation of the sheath.
Figure 40:
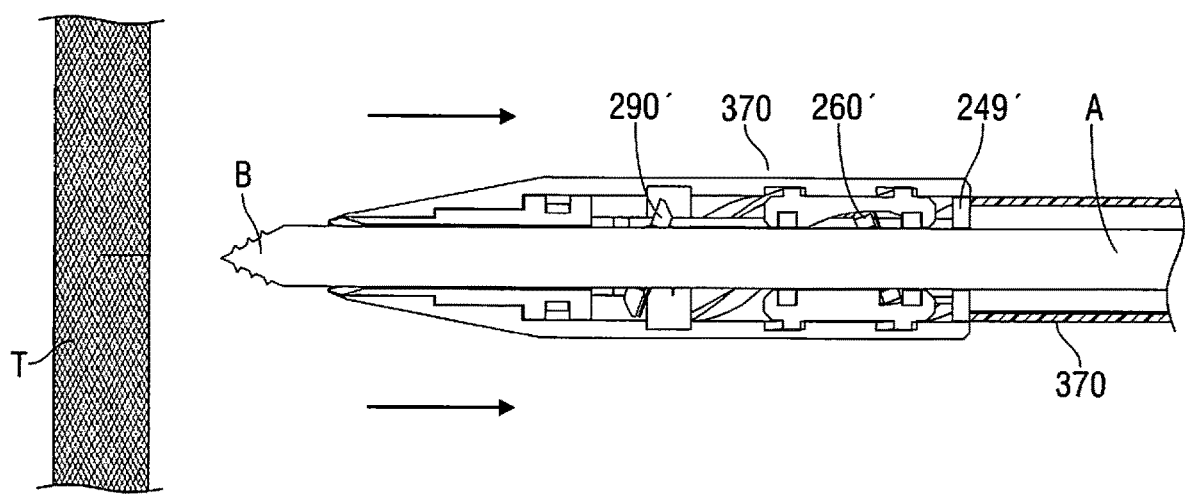
FIG. 40 is a side view similar to FIG. 39 showing removal of the flexible sheath, lead extractor and lead from the body.

In an alternate embodiment illustrated in FIGS. 37-40, a flexible sheath 370 is provided which enables unscrewing of the lead at the distal end. The sheath 370 also has sufficient rigidity to allow for rotation. The lead extractor 200' is the same as lead extractor 200 except for the provision of the sheath positioned over a portion of the extractor 200'. The extractor 200' is used in the identical fashion as extractor 200 described above to separate the lead from the tissue encapsulating the lead along its length. Therefore, for brevity, the components of the extractor 200' and their function will not be repeated herein as they are identical to extractor 200, and identical components, e.g., outer housing 202', distal clamping ring 290', and proximal clamping ring 260' are labeled with "prime" designations. The sheath 370 is attached to the proximal end cap 249' of the inner tube 204' and extends proximally of the end cap 249', forming an extension of the inner tube 204'. After the extractor 200' has completed its tunneling action as described above and the lead A is free from tissue proximal to its embedded distal end, the flexible sheath 370 is rotated (FIG. 38), which in turn rotates the extractor 200'. Since the lead A is firmly clamped by the extractor 200', rotation of the sheath 370 also rotates the lead A, thereby unscrewing the distal tip B of the lead A which is embedded in tissue (FIG. 39). The sheath 370, extractor 200' and clamped lead A can then be removed from the body as shown in FIG. 40.

Although described for extracting a lead, the extractors of the present disclosure can also be utilized in other surgical applications.

While specific embodiments have been described above, it will be appreciated that the invention may be practiced otherwise than as described. Moreover, specific items discussed with reference to any of the isolated drawings may freely be inter-changed supplementing each outer in any particular way. The descriptions above are intended to be illustrative, not limiting. Thus, it will be apparent to one skilled in the art that modifications may be made to the invention as described in the foregoing without departing from the scope of the claims set out below.

What is claimed is:

1. An extractor for removing an implanted lead from a patient, the extractor comprising a longitudinal axis, a proximal portion, a distal portion, a lumen dimensioned to receive the lead therein, a cutter at the distal portion for cutting tissue adjacent the implanted lead, a first clamp configured to apply a clamping force to the lead and spaced proximally of the cutter, and a second clamp configured to apply a clamping force to the lead and axially spaced from the first clamp, the first clamp movable between a clamping position to clamp the lead and an unclamping position to unclamp the lead, and the second clamp movable between a clamping position to clamp the lead and an unclamping position to unclamp the lead, the extractor and lead being relatively movable to remove the lead, wherein the first clamp is movable axially toward and away from the second clamp to alter an axial distance between a distalmost end of the first and second clamps so the axial distance from the distalmost end of the first clamp to a distalmost end of the second clamp differs in first and second positions of the first clamp.

2. The extractor of claim 1, further comprising an actuator operatively associated with the first clamp, wherein movement of the actuator between proximal and distal positions alters an orientation of the first clamp to move it between the clamping and unclamping positions.

3. The extractor of claim 1, wherein the first clamp is positionable in the clamped position while the second clamp is positionable in the unclamped position.

4. The extractor of claim 3, wherein the second clamp is pivotable relative to the longitudinal axis of the lead to apply a clamping force on the lead to clamp the lead, wherein the first and second clamps are alternatively movable between the clamped and unclamped positions so that the first clamp clamps the lead while the second clamp is in an unclamped position to allow relative movement of the extractor and lead and the second clamp clamps the lead while the first clamp is in an unclamped position to allow relative movement of the extractor and lead.

5. The extractor of claim 1, wherein the first clamp has a first hinge and the second clamp has a second hinge and the first and second clamps tilt toward each other, the first and second hinges radially spaced from a longitudinal axis of the extractor and lying on opposing sides of the longitudinal axis of the extractor.

6. The extractor of claim 1, further comprising a cable operatively associated with the first clamp, wherein distal movement of the cable advances the first clamp distally and proximal movement of the cable retracts the first clamp proximally.

7. The extractor of claim 1, further comprising a stop to limit distal travel of the first clamp, wherein the stop can be overridden to release the first and second clamps.

8. The extractor of claim 1, wherein the cutter is both axially movable and rotatable concurrently in response to axial movement of the first clamp.

9. The extractor of claim 1, wherein an entirety of the first clamp is axially spaced from an entirety of the second clamp.

10. An extractor for removing an implanted lead from a patient, the extractor comprising a proximal portion, a distal portion, a lumen to receive the lead therein, a first clamp configured to apply a clamping force to the lead and movable between unclamped and clamped positions, and a rotatable tissue cutter at the distal portion configured for cutting tissue adjacent the implanted lead, the extractor and lead incrementally relatively movable to swallow the lead as tissue is cut by the tissue cutter adjacent the lead, wherein axial movement of the first clamp automatically and concurrently rotates the tissue cutter about a longitudinal axis, wherein the tissue cutter is formed on an outer housing of the extractor and the extractor includes an inner housing positioned within the outer housing, and the outer housing has an internal helical slot and is rotatable relative to the inner housing.

11. The extractor of claim 10, further comprising a second clamp configured to apply a clamping force to the lead and movable between unclamped and clamped positions, wherein relative movement of the lead and extractor causes pivoting of the first and second clamps.

12. The extractor of claim 10, wherein the first clamp has a plurality of teeth engageable with the lead.

13. The extractor of claim 10, wherein the tissue cutter is formed on an outer housing of the extractor and the extractor includes an inner housing positioned within the outer housing, and the outer housing has an internal helical slot and is rotatable relative to the inner housing.

14. The extractor of claim 13, wherein the inner housing has a cutting portion interacting with the tissue cutter of the outer housing.

15. An extractor for removing an implanted lead from a patient, the extractor comprising:
a lumen dimensioned to receive the lead therein;
a tissue cutter at a distal portion, the tissue cutter configured for cutting tissue adjacent the lead;
a distal clamp configured to selectively engage and clamp an external surface of the lead when the lead is positioned within the lumen, the distal clamp spaced proximally of the cutter;
a proximal clamp configured to selectively engage the external surface of the lead when the lead is positioned within the lumen, the proximal clamp spaced proximally of the distal clamp, the proximal clamp movable axially with respect to the distal clamp for extraction of the lead from the patient, the proximal clamp movable axially between positions closer and further from the distal clamp, wherein an entirety of the proximal clamp is proximal of an entirety of the distal clamp.

16. The extractor of claim 15, further comprising a comprising a cable operatively associated with the proximal clamp, the cable movable between first and second positions to move the proximal clamp between distal and proximal positions.

17. The extractor of claim 15, wherein movement of the proximal clamp proximally effects extraction of the lead as the extractor is advanced distally over the lead and movement of the proximal clamp distally resets the proximal clamp for subsequent proximal movement of the proximal clamp for further extraction of the lead.

18. The extractor of claim 15, wherein the distal clamp is substantially stationary as the proximal clamp moves between distal and proximal directions.

19. The extractor of claim 15, further comprising a first spring for biasing the distal clamp and a second spring for biasing the proximal clamp.

20. The extractor of claim 15, further comprising a carrier slidable axially between proximal and distal positions to carry the proximal clamp between proximal and distal positions, and the cutter is rotatable in response to axial movement of the carrier.

* * * * *